(12) United States Patent
Qiu et al.

(10) Patent No.: US 10,408,777 B2
(45) Date of Patent: Sep. 10, 2019

(54) DENSITY MEASUREMENT SYSTEM AND METHOD

(71) Applicant: Industrial Tomography Systems PLC, Manchester (GB)

(72) Inventors: Changhua Qiu, Manchester (GB); Kenneth Primrose, Manchester (GB)

(73) Assignee: Industrial Tomography Systems PLC, Manchester (GB)

(*) Notice: Subject to any disclaimer, the term of this patent is extended or adjusted under 35 U.S.C. 154(b) by 249 days.

(21) Appl. No.: 15/510,363

(22) PCT Filed: Sep. 11, 2015

(86) PCT No.: PCT/GB2015/052643
§ 371 (c)(1),
(2) Date: Mar. 10, 2017

(87) PCT Pub. No.: WO2016/038391
PCT Pub. Date: Mar. 17, 2016

(65) Prior Publication Data
US 2017/0241929 A1 Aug. 24, 2017

(30) Foreign Application Priority Data
Sep. 12, 2014 (GB) .................................. 1416182.2

(51) Int. Cl.
*G01N 9/00* (2006.01)
*G01N 27/04* (2006.01)
(Continued)

(52) U.S. Cl.
CPC ............... *G01N 27/04* (2013.01); *G01N 9/00* (2013.01); *G01N 27/026* (2013.01);
(Continued)

(58) Field of Classification Search
CPC ............. G01N 33/26–32; G01N 27/04; G01N 27/026; G01N 33/2823; G01N 9/00;
(Continued)

(56) References Cited

U.S. PATENT DOCUMENTS

| 4,617,939 A | 10/1986 | Brown |
| 5,272,624 A | 12/1993 | Gisser |

(Continued)

FOREIGN PATENT DOCUMENTS

| EP | 2343539 A1 | 7/2011 |
| GB | 2507368 A | 4/2014 |

(Continued)

OTHER PUBLICATIONS

United Kingdom Patent Office Search Report for Application No. 1416182.2 dated Mar. 6, 2015 (4 pages).

(Continued)

*Primary Examiner* — Robert R Raevis
(74) *Attorney, Agent, or Firm* — Michael Best & Friedrich LLP

(57) ABSTRACT

A density measurement system for measuring the density of a material within a region, the density measurement system comprises: a plurality of electrodes arranged around the region; an energization source arranged to apply an electrical signal to at least one of said electrodes; a monitor arranged to monitor an electrical parameter at at least one of said electrodes, the monitored electrical parameter being caused to change in response to flow of electrical current within the region; and a processor arranged to: generate data indicative of the complex impedance of the material within the region based upon the monitored electrical parameter; and generate data indicative of the density of the material based upon the data indicative of the complex impedance of the material.

20 Claims, 13 Drawing Sheets

(51) Int. Cl.
*G01N 27/02* (2006.01)
*G01N 33/28* (2006.01)
*G05D 7/06* (2006.01)
*G01N 11/00* (2006.01)
*E02F 5/00* (2006.01)

(52) U.S. Cl.
CPC ....... *G01N 33/2823* (2013.01); *G05D 7/0617* (2013.01); *E02F 5/006* (2013.01); *G01N 2011/0066* (2013.01)

(58) Field of Classification Search
CPC ......... G01N 2011/0066; G01N 11/006; G05D 7/0617; E02F 5/006
USPC .......................................................... 73/32 R
See application file for complete search history.

(56) References Cited

U.S. PATENT DOCUMENTS

| | | | |
|---|---|---|---|
| 5,588,429 | A | 12/1996 | Isaacson |
| 2013/0144548 | A1 | 6/2013 | Xie |

FOREIGN PATENT DOCUMENTS

| | | | |
|---|---|---|---|
| JP | 2012202924 A | | 10/2012 |
| JP | 2013-195343 | * | 9/2013 |
| WO | 2002103376 A1 | | 12/2002 |
| WO | WO-2006044868 A1 | | 4/2006 |
| WO | WO-2010150009 A1 | | 12/2010 |
| WO | 2011039416 A1 | | 4/2011 |
| WO | WO-2014191991 A1 | | 12/2014 |

OTHER PUBLICATIONS

International Search Report and Written Opinion for Application No. PCT/GB2015/052643 dated Jan. 26, 2016 (18 pages).

Giguere R et al: "Characterization of slurry flow regime transitions by ERT", Chemical Engineering Research and Design, Part A, Institution of Chemical Engineers, XX, vol. 86, No. 9, Sep. 1, 2008 (Sep. 1, 2008), pp. 989-996, XP023980366, ISSN: 0263-8762, DOI: 10.1016/J.CHERD.2008.03.014 [retrieved on May 22, 2008].

H. Nasr-El-Din et al: "A conductivity probe for measuring local concentrations in slurry systems", International Journal of Multiphase Flow., vol. 13, No. 3, May 1, 1987 (May 1, 1987), pp. 365-378, XP055226170, NL ISSN: 0301-9322, DOI: 10.1016/0301-9322 (87) 90055-3 abstract p. 367, Bruggeman's equation.

Xiang Deng et al: "Fusion Research of Electrical Tomography with others Sensors for Two-phase Flow Measurement", Measurement Science Review, vol. 12, No. 2, Jan. 1, 2012 (Jan. 1, 2012), XP055135675, ISSN: 1335-8871, DOI: 10.2478/v10048-012-0008-7 Abstract; figures 4, 5, 6, 7, paragraph "3. Fusion of ECT With ERT".

* cited by examiner

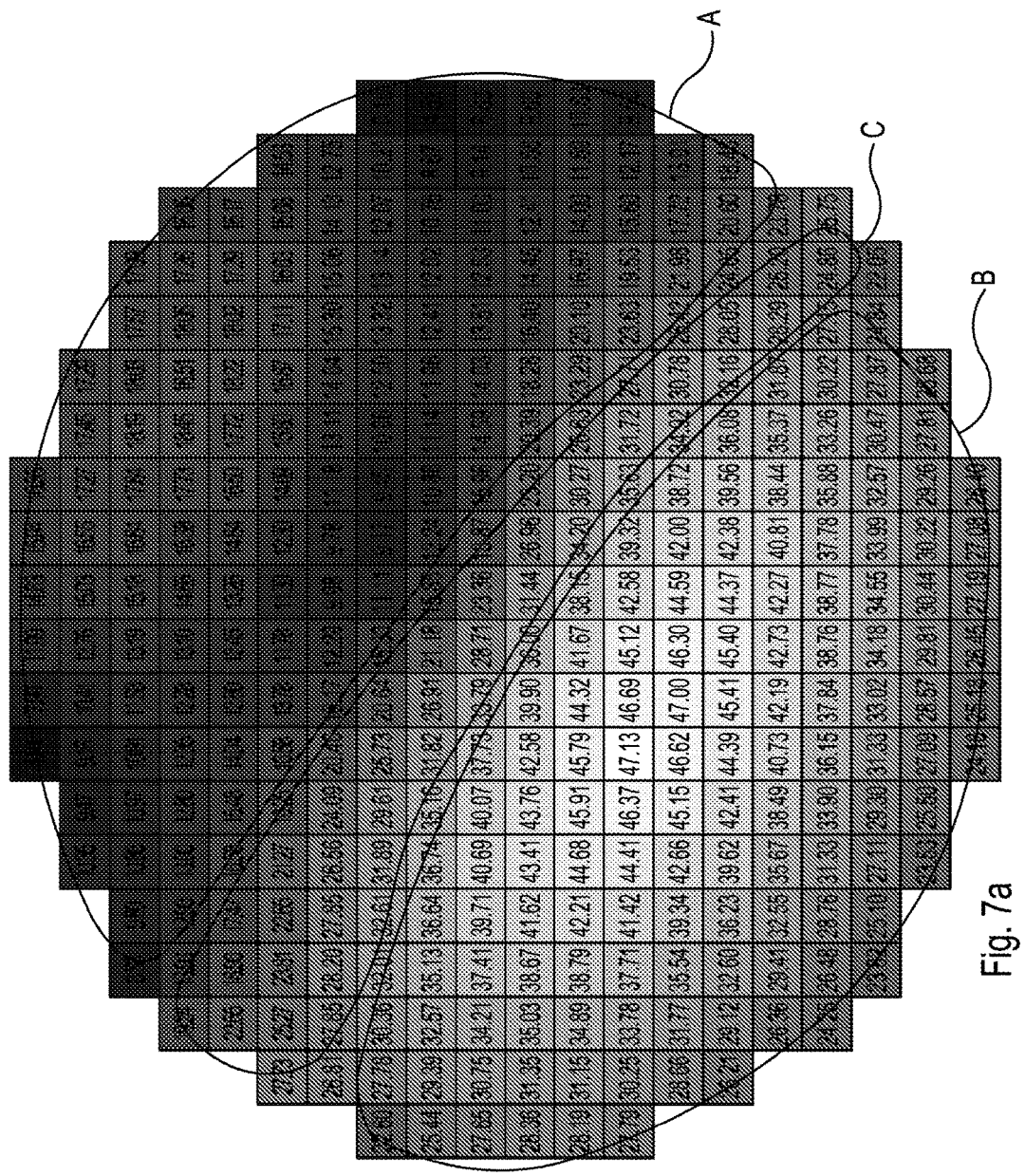

DENSITY MEASUREMENT SYSTEM AND METHOD

The present invention relates to a measurement system and method. More particularly, but not exclusively, the invention relates to a measurement system and apparatus for measuring the slurry density of slurry within in region of interest, such as, for example, within a pipe.

Many industrial, environmental and marine engineering systems rely on the transport of solid particulate-fluid mixtures within pipes. For example, hydraulic conveying can be applied to raw minerals and manufactured products. Further examples of solid-particulate-fluid mixtures are sewage, waste disposal and waste treatment. Solid particulates are any material which comprises discrete particles, each particle having a physical boundary and each particle being small in relation to its environment (e.g. a grain of sand within a pipeline having a diameter of one meter). Solid particulates may be dense and non-porous, such as, for example grains of mineral or rock. Alternatively, solid particulates may be semi-soft and porous, such as for example aggregates or biological flocs). The fluids within such mixtures may be gas, liquid gas, aqueous or non-aqueous continua. In many industrial applications fluids are aqueous. Such mixtures may be referred to as slurries.

Knowledge of the proportion of solid material within such a mixture can allow the volume of solid material transported to be monitored and controlled. By periodically sampling the mixture, and measuring the contents of the samples, an estimate can be made of the mass of solid material within the samples, and thus the density of the material. The density of the material may be referred to as slurry density. This can be used to estimate the mass within the mixture. However, non-uniform distribution of solids within a mixture, and a fraction of solids which changes with time may result in any such sampling providing an estimate of limited accuracy.

One way of achieving a more accurate measure of the density of a mixture is by use of a density measurement system. Known density measurement systems typically make use of interactions (such as scattering) between radiation and material within a region of interest. An example of such a density measurement system is a gamma densitometer. A beam of gamma radiation is directed at the region of interest. A material having a high density will result in more scattering of the beam of gamma radiation than a material having a low density. The proportion of gamma radiation that passes through the material and is not scattered is measured and this measurement used to estimate the material density. However, gamma radiation is typically produced by a radioactive source, such as one based on caesium. As such, gamma densitometry may present an environmental hazard by virtue of the radioactive source.

It is an object of the present invention to provide a slurry density measurement system which overcomes one or more of the problems associated with known density measurement systems, discussed above or otherwise.

According to a first aspect of the invention there is provided a density measurement system for measuring the density of a material within a region, the density measurement system comprising: a plurality of electrodes arranged around the region; an energisation source arranged to apply an electrical signal to at least one of said electrodes; a monitor arranged to monitor an electrical parameter at at least one of said electrodes, the monitored electrical parameter being caused to change in response to flow of electrical current within the region; and a processor arranged to: generate data indicative of the complex impedance of the material within the region based upon the monitored electrical parameter; and generate data indicative of the density of the material based upon the data indicative of the complex impedance of the material.

The generating of data indicative of the complex impedance of the material within the region based upon the monitored electrical parameter allows data indicative of the density of the material to be generated accurately. The use of complex impedance (or complex conductivity), allows the effect of the material on both the magnitude of the monitored electrical parameter and the phase of the monitored electrical parameter to be used to improve the accuracy of any measurement, for example, by taking into account the frequency response of the material. While some materials will have an impedance (or conductivity) which does not vary with frequency, many materials will respond differently to an AC energisation based upon its frequency. Monitoring this response allows accurate information to be gathered regarding the impedance of the material, and also allows accurate information regarding the proportion of a first component within the material to be generated.

The density may be referred to as a slurry density. The material may be referred to as a slurry. Where the term slurry is used to refer to a mixture of solids and liquid, the slurry density is understood to be the effective density of the mixture of solids and liquid. The region may suitably be bounded by a pipe. The pipe may suitably have a circular cross-section. The pipe may suitably have a diameter of up to 1.2 m. The pipe may suitably have a diameter of greater than 50 mm.

The density measurement system may comprise at least 4 electrodes. The density measurement system may comprise at least 8 electrodes. The density measurement system may comprise 16 electrodes. The electrodes may be evenly distributed around the region.

Generating data indicative of the complex impedance of the material may be further based upon reference data, said reference data comprising an expected value of the monitored electrical parameter, the expected value being based upon a reference material having a predetermined electrical characteristic affecting said electrical parameter.

The use of reference data allows the effect of measurement artefacts, such as, for example, those caused by electrode size and position, and electrode surface condition, to be reduced. The reference data, which may, for example, be generated based on a reference material having a known complex impedance, allows data indicative of the complex impedance of the material to be accurately calculated.

Generating data indicative of the density of the material based upon the monitored electrical parameter may comprise generating data indicative of the relative difference between the monitored electrical parameter and the expected value of the monitored electrical parameter.

Generating data indicative of the complex impedance of the material based upon the monitored electrical parameter may comprise generating data indicative of the relative impedance of the material compared to the reference material.

Generating data indicative of the density of the material based upon the data indicative of the complex impedance of the material may comprise: generating data indicative of the concentration of a first component within the material based upon the complex impedance of the material and the complex impedance of the first component.

Generating data indicative of the density of the material may be further based upon the complex impedance of a second component.

Generating data indicative of composition of the material may comprise generating data indicative of the modulus of the complex impedance of the material.

Taking the modulus of the complex impedance of the material allows both real and imaginary components of the impedance to be taken into account. This may be of particular benefit where a material comprises a mixture of components which respond differently at different frequencies, allowing both components to contribute to any calculation of the density of the material. Where only real or imaginary components are considered, the presence of once component may be underestimated, overestimated, or even entirely neglected.

The density measurement system may further comprise at least one sensor arranged to generate data indicative of a property of the material within the region, wherein generating data indicative of the density of the material within the region is further based upon the data indicative of a property of the material.

The sensor may be a temperature sensor. The sensor may be a conductivity sensor.

The density measurement system may further comprise a gas fraction probe, the gas fraction probe being configured to generate data indicative of the proportion of gas within the region.

The use of a gas fraction sensor allows an improved estimate of density to be calculated which takes into account any entrained gas (e.g. air) within the material.

The gas fraction probe may comprise an ultrasound detector.

The data indicative of the density of the material may be generated based upon the data indicative of the proportion of gas within the region.

The data indicative of the density of the material may comprise a plurality values, each value being associated with a respective one of a plurality of sub-regions within the region.

The data indicative of the density of the material may comprise a spatial average of a plurality of values, each of the plurality of values being associated with a respective one of a plurality of sub-regions within the region.

The energisation source may be arranged to apply an alternating electrical signal between at least a first pair of said electrodes.

The monitor may be arranged to monitor a potential difference between at least a second pair of said electrodes, whilst the electrical signal is applied between the first pair of said electrodes.

The monitor may be further arranged to monitor a potential difference between at least a third pair of said electrodes, whilst the electrical signal is applied between the first pair of said electrodes, at a different time to the monitoring of the potential difference between the second pair of electrodes.

The energisation source may be further arranged to apply an alternating electrical signal between a further pair of said electrodes, the electrical signal being applied between the further pair of said electrodes at a different time to the electrical signal being applied between the first pair of said electrodes.

According to a second aspect of the invention there is provided a method for measuring the density of a material within a region, the method comprising: providing a plurality of electrodes around the region; an energisation source; a monitor; and a processor; applying an electrical signal to at least one of said electrodes by the energisation source; monitoring an electrical parameter at at least one of said electrodes, the electrical parameter being caused to change in response to flow of electrical current within the region; generating, by the processor, data indicative of the complex impedance of the material within the region based upon the monitored electrical; and generating data indicative of the density of the material based upon the data indicative of the complex impedance of the material.

Generating data indicative of the complex impedance of the material may be further based upon reference data, said reference data comprising an expected value of the monitored electrical parameter, the expected value being based upon a reference material having a predetermined electrical characteristic affecting said electrical parameter.

Generating data indicative of the density of the material based upon the monitored electrical parameter may comprise generating data indicative of the relative difference between the monitored electrical parameter and the expected value of the monitored electrical parameter.

Generating data indicative of the complex impedance of the material based upon the monitored electrical parameter may comprise generating data indicative of the relative impedance of the material compared to the reference material.

Generating data indicative of the density of the material based upon the data indicative of the complex impedance of the material may comprise: generating data indicative of the concentration of a first component within the material based upon the complex impedance of the material and the complex impedance of the first component.

Generating data indicative of the density of the material may be further based upon the complex impedance of a second component.

Generating data indicative of composition of the material may comprise generating data indicative of the modulus of the complex impedance of the material.

The method may further comprise: providing at least one sensor; and generating, by the sensor, data indicative of a property of the material within the region, wherein generating data indicative of the density of the material within the region, by the processor, is further based upon the data indicative of a property of the material.

The sensor may be a temperature sensor. The sensor may be a conductivity sensor.

The method may further comprise: providing a gas fraction probe; and generating, by the gas fraction probe, data indicative of the proportion of gas within the region.

The gas fraction probe may comprise an ultrasound detector.

The data indicative of the density of the material may be generated by the processor based upon the data indicative of the proportion of gas within the region.

The data indicative of the density of the material may comprise a plurality values, each value being associated with a respective one of a plurality of sub-regions within the region.

The data indicative of the density of the material may comprise a spatial average of a plurality of values, each of the plurality of values being associated with a respective one of a plurality of sub-regions within the region.

The method may comprise: applying, by the energisation source, an alternating electrical signal between at least a first pair of said electrodes.

The method may comprise monitoring, by the monitor, a potential difference between at least a second pair of said electrodes, whilst the electrical signal is applied between the first pair of said electrodes.

The method may further comprise monitoring, by the monitor, a potential difference between at least a third pair of said electrodes, whilst the electrical signal is applied between the first pair of said electrodes, at a different time to the monitoring of the potential difference between the second pair of electrodes.

The method may further comprise applying, by the energisation source, an alternating electrical signal between a further pair of said electrodes, the electrical signal being applied between the further pair of said electrodes at a different time to the electrical signal being applied between the first pair of said electrodes.

According to a further aspect of the invention there is provided a method of controlling an industrial process, the method further comprising a method according the second aspect of the invention, wherein the industrial process is controlled based upon the data indicative of the density of the material.

According to another aspect of the invention there is provided an industrial processing apparatus, the industrial processing apparatus comprising a density measurement system according to the first aspect of the invention.

According to a yet further aspect of the invention there is provided a method of hydraulic conveying, the method further comprising a method according the second aspect of the invention, wherein the hydraulic conveying is controlled based upon the data indicative of the density of the material. The hydraulic conveying may be carried out by a dredging apparatus.

According to another aspect of the invention there is provided a hydraulic conveying apparatus, the hydraulic conveying apparatus comprising a density measurement system according to the first aspect of the invention. The hydraulic conveying apparatus may be a dredging apparatus.

According to a yet further aspect of the invention, there is provided a density measurement system for measuring the density of a material within a region, the density measurement system comprising: a plurality of electrodes arranged around the region; an energisation source arranged to apply an electrical signal to at least one of said electrodes; a monitor arranged to monitor an electrical parameter at at least one of said electrodes, the monitored electrical parameter being caused to change in response to flow of electrical current within the region; and a processor arranged to generate data indicative of the density of the material within the region based upon the monitored electrical parameter and reference data, said reference data comprising an expected value of the monitored electrical parameter, the expected value being based upon a reference material having a predetermined electrical characteristic affecting said electrical parameter.

Generating data indicative of the density of the material may be based upon data indicative of the impedance of the material. Data indicative of the impedance of the material may be generated based upon the monitored electrical parameter.

The density measurement system may thus be arranged to use either electrical resistivity tomography, or electrical impedance tomography. The impedance is preferable complex impedance. The density measurement system is capable of taking into account both real and imaginary components of the complex impedance.

The data indicative of the density of the material may be based upon the real component of impedance, the imaginary component of impedance, or the combination of both the real and the imaginary components of impedance. There are certain benefits in certain applications for using either one or both of the impedance components, which are described in more detail below.

According to a yet further aspect of the invention there is provided a method for generating data indicating a distribution of matter within a region, the method comprising: obtaining first data indicating a property of matter within said region; obtaining second data based upon a reference pattern of matter within the region; and combining said first and second data to generate said data indicating a distribution of matter within the region.

By combining first data indicating a property (e.g. conductivity) of matter within said region and second data based upon a reference pattern it is possible to identify various different portion of the region which have different characteristics, and to treat the data indicating a property of matter within those portions differently. For example, where a slurry is flowing within a pipe, the flow may be stratified such that slurry flows at the bottom of the pipe, air is present at the top of the pipe, and an interface is present between the slurry and air. However, conductivity data alone may not accurately reflect this distribution of material. For example, regions of high solids (e.g. slurry) and air may both exhibit lower conductivity than regions of liquid (i.e. low solid or interface between slurry and air). As such by using the second data (e.g. a mask) to identify the various portions within the region, the second data being based upon reference data which may, for example, indicate a normal flow pattern, conductivity data relating to each portion can be either disregarded, scaled, or taken into account as appropriate so as to provide an accurate indication of the distribution of matter.

The reference pattern may be based upon prior knowledge of normal or regular flow patterns. The reference pattern can thus be used to identify various portions of the region, or flow regions, which correspond to regions which are known to contain a particular component (e.g. slurry or air) based upon the prior knowledge that those components will occupy a particular location within the region (e.g. slurry at the bottom of the pipe, air at the top of the pipe).

The second data may be based upon an orientation of the region.

Obtaining the second data may comprise generating said second data based upon the first data and the reference pattern. Optionally the second data may be generated automatically.

The first data may comprise a plurality of first data items, each of the plurality of first data items indicating the property of matter at respective one of a plurality of locations within the region.

The reference pattern may comprise data indicating a plurality of portions of the region, each portion comprising one or more locations within the region.

For example, a first portion may be a slurry region which comprises a slurry. Similarly, a second portion may be an air region, which comprises air. Further, a third portion may be an interface region, which comprises an interface between the slurry and air regions.

The second data may comprise a plurality of second data items, each of the plurality of second data items being associated with a respective one or more of the plurality of locations within the region, each of the plurality of second data items being based upon a relationship between a corresponding first data item and the reference pattern.

Each of the plurality of second data items may be associated with a respective one of the plurality of locations within the region. Each of the plurality of second data items may be associated with a respective one of the plurality of first data items Each of the plurality of second data items may comprise a scaling factor, and combining the first and second data may comprise multiplying each of the first data items by a corresponding one of the second data items so as to generate said data indicating a distribution of matter within the region.

Generating the second data based upon the first data and the reference pattern may comprise assigning a predetermined scaling factor to each of the second data items based upon the relationship between a corresponding first data item and the reference pattern.

The method may further comprise generating data indicative of variation in first data item values within a predetermined part of the region, and generating the second data based upon said data indicative of variation.

Said data indicative of variation in first data item values within a predetermined part of the region may be based upon average data items, each average data item being indicative of the property of matter in a predetermined subset of locations within the region.

The distribution data may comprise a plurality of distribution data items, each of the plurality of distribution data items being associated with a respective one or more of the plurality of locations within the region.

The method may further comprise generating an average of the distribution data items. The method may further comprise generating an average of the distribution data items which correspond to locations within a predetermined subset of the plurality of portions of the region.

The method may further comprise scaling the generated average based upon the proportion of the region contained within the predetermined subset of the plurality of portions of the region.

The region may be defined by a pipe.

Data indicating a distribution of matter within the region may comprise data indicating volumetric concentration of a material flowing within the region.

The property of matter may be the complex impedance of matter.

The property of matter may be the volumetric concentration of a predetermined material.

The method may further comprising generating data indicating density of slurry within the region based upon the data indicating a distribution of matter within the region.

According to a yet further aspect of the invention there is provided an apparatus arranged to perform a method according to any of the above described aspects of the invention.

It will of course be appreciated that features described above with reference to one aspect of the invention may be combined with other aspects of the invention.

Embodiments of the invention will now be described, by way of example only, with reference to the accompanying drawings, in which:

FIGS. 7a and 7b show representations of conductivity data captured by a measurement system as shown in FIG. 1;

FIGS. 8a and 8b show representations of data generated by a measurement system as shown in FIG. 1;

Figure 1:
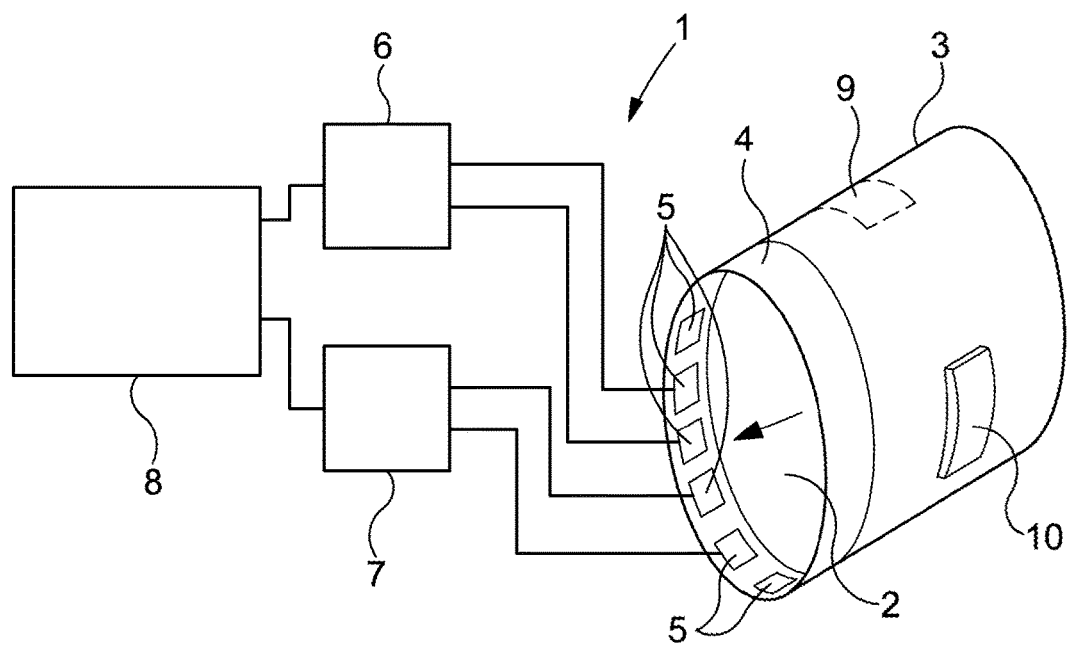
FIG. 1 shows a measurement system according to an embodiment of the invention.
Figure 7B:
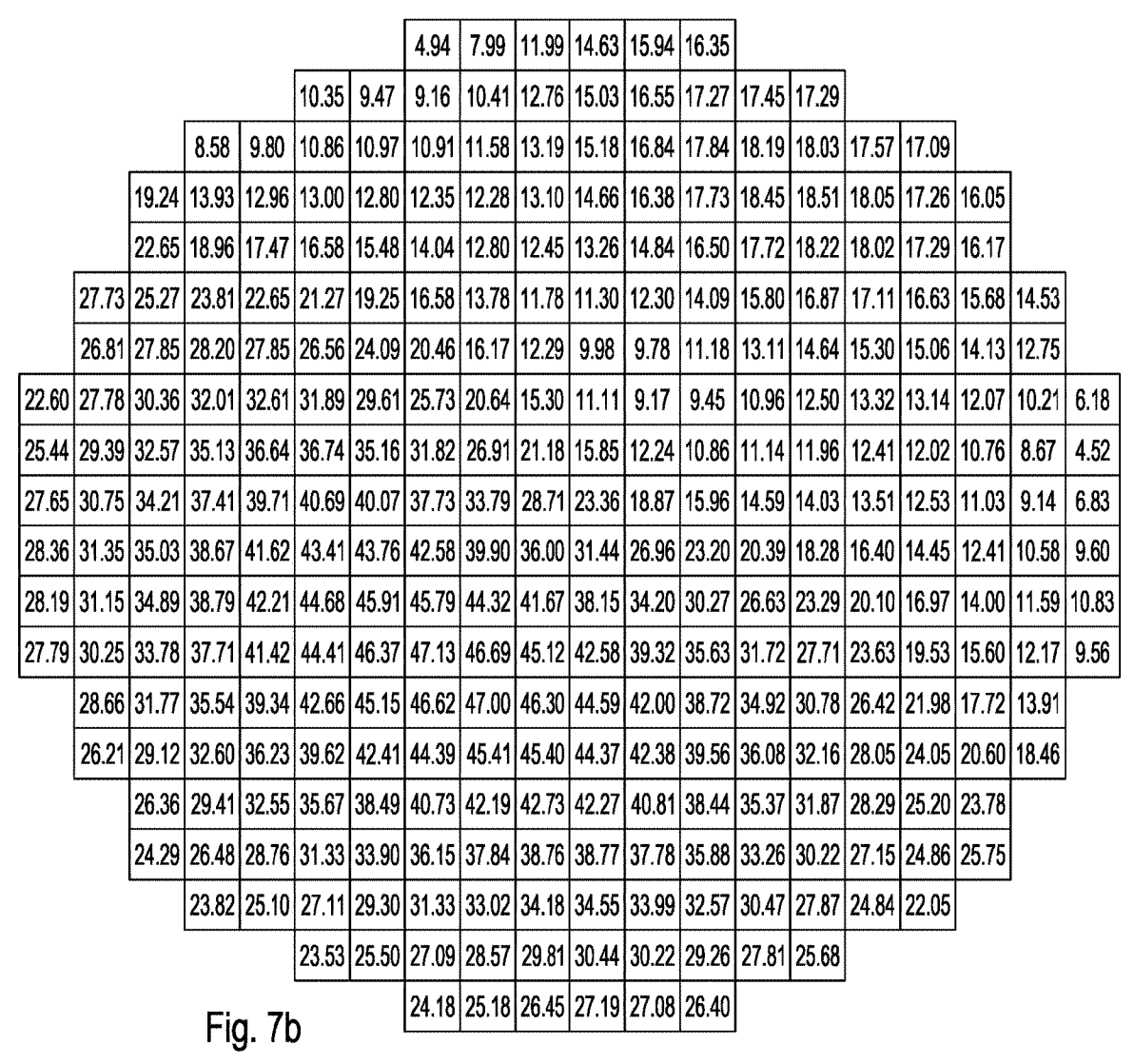
Figure 9A:
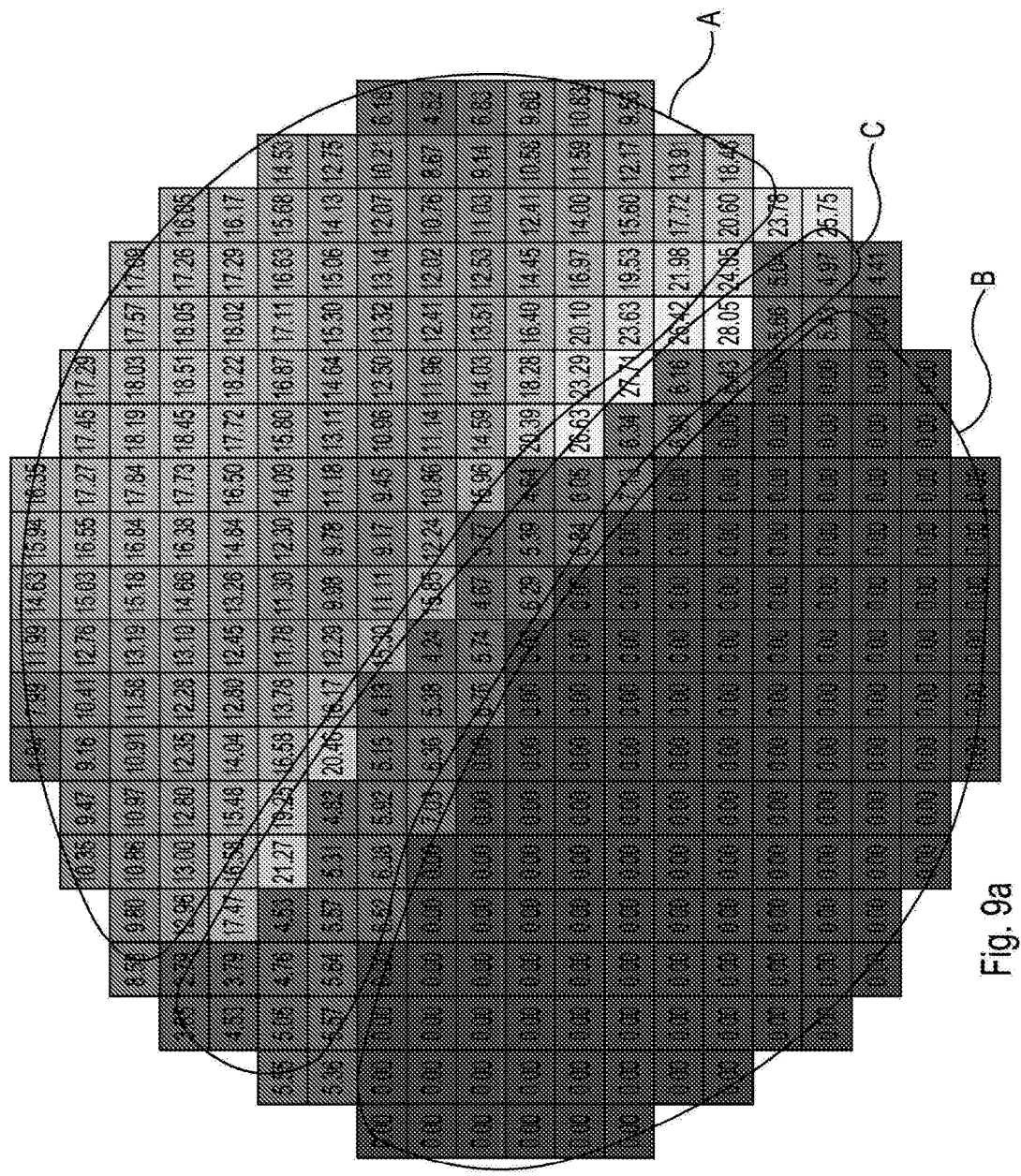
Figure 9B:
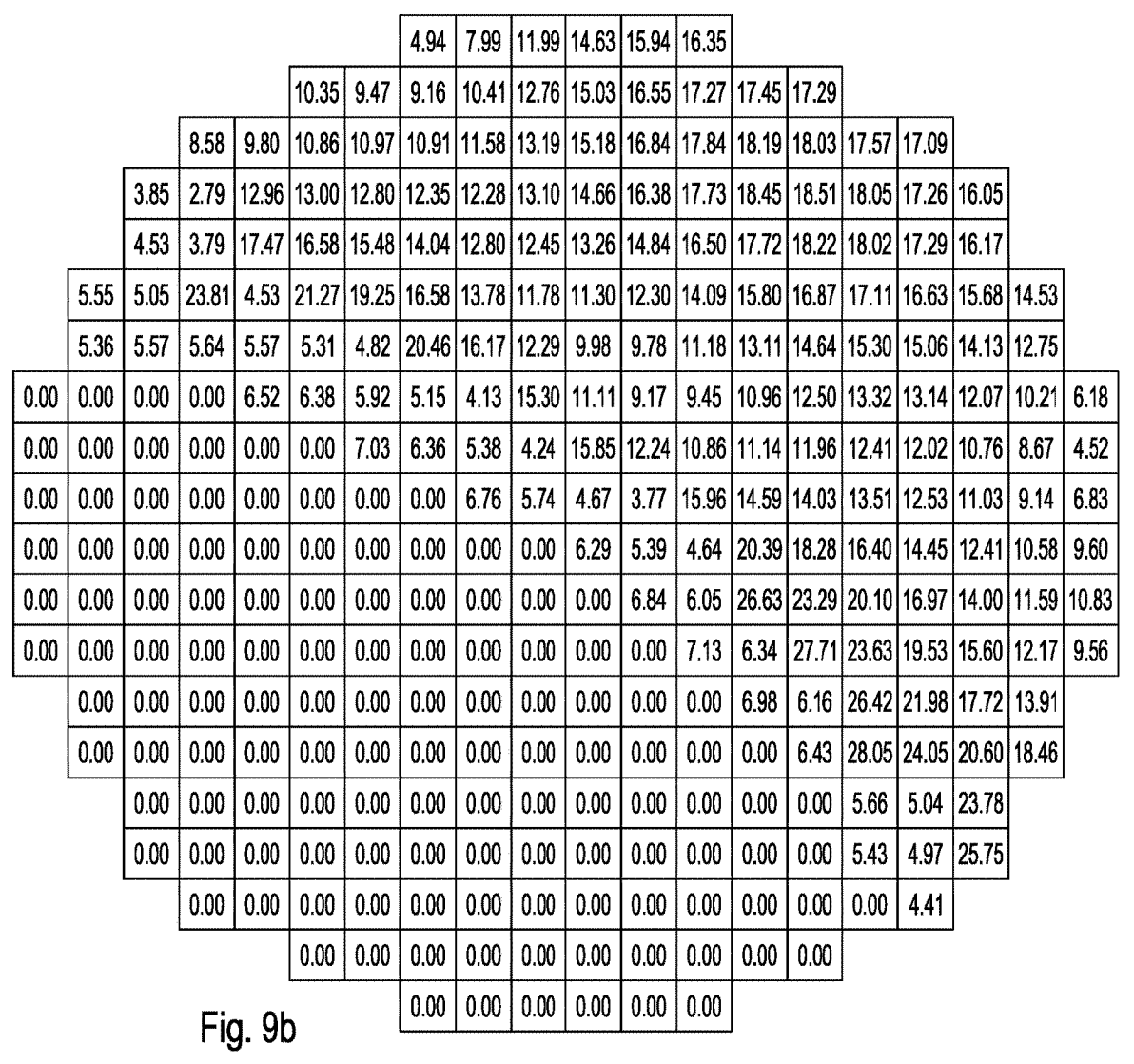
Figure 10:
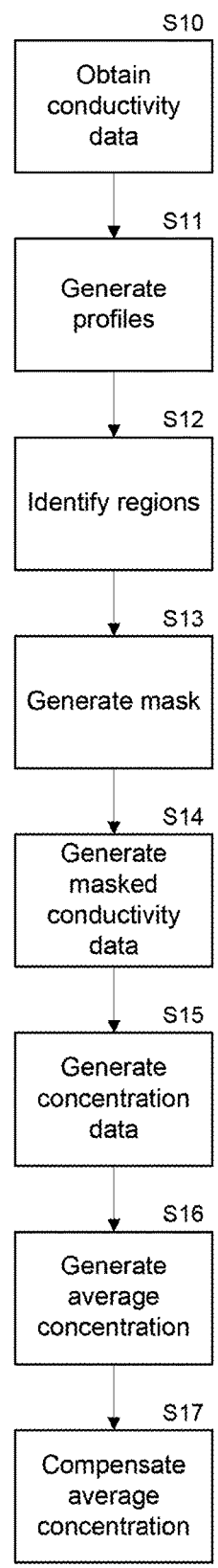
Figure 11A:
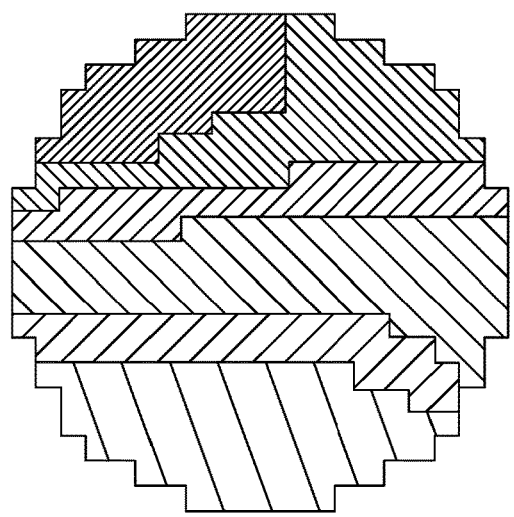
Figure 11B:
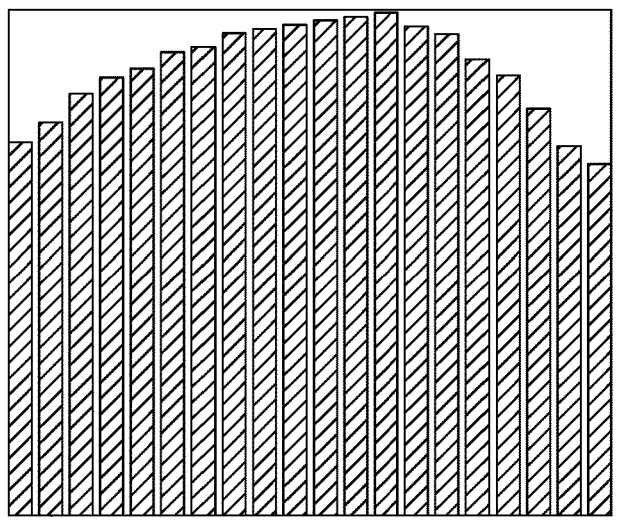
Figure 11C:
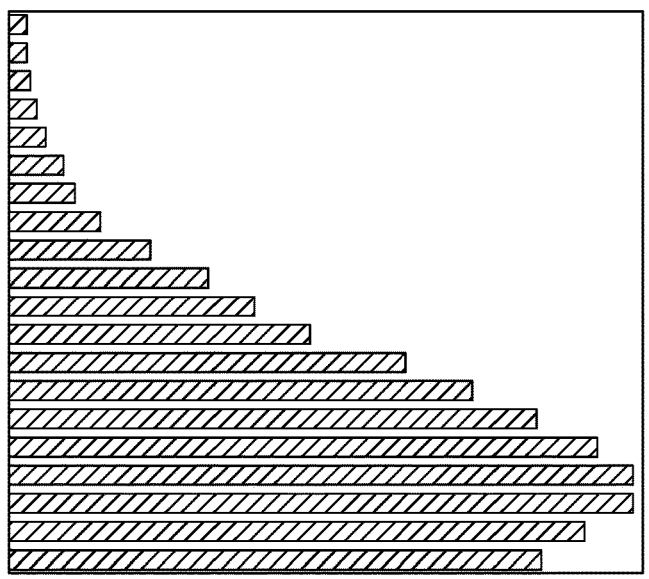

FIGS. 9a and 9b show representations of data generated by combination of the data shown in FIGS. 7a and 7b with 8a and 8b;

FIG. 10 shows a process carried out by the measurement system shown in FIG. 1 to generate the data shown in FIGS. 9a and 9b; and FIGS. 11a to 11c show representations of data used during the processing of FIG. 10.

Referring to FIG. 1, a measurement system 1 is shown. The measurement system 1 is arranged to measure the density of a material 2 flowing within a pipe 3. The material 2 is a mixture of liquid and solid components. The measurement system 1 comprises an electrical impedance tomography (EIT) sensor 4. The EIT sensor 4 has a plurality of electrodes 5.

The pipe 3, may, for example, form part of a hydraulic conveying apparatus, such as a hydraulic dredging apparatus. Such a hydraulic dredging apparatus is configured to transport large volumes of solid particulates from a sea-bed, for example, to assist with land formation, or to maintain navigation channels. The hydraulic dredging apparatus is mounted on a dredging barge which is navigated over areas which require dredging. Knowledge of the volume and mass of solid particulates transported by the dredging apparatus allow efficient navigation and control of the dredging barge. For example, by measuring the mass of solid particulates within the slurry, the rate of dredging may be increased or decreased to allowing a predetermined solid particulate flow rate, or total mass of solid to be removed from a sea-bed. Alternatively, density measurement may be used to identify when the dredging apparatus should be configured differently, for example, where the solid particulate fraction within the slurry drops below a predetermined threshold.

Where the density measurement system 1 is used with in conjunction with a dredging apparatus, the material 2 may be, for example, primarily a mixture of sand (solid component) and saline water (liquid component). The pipe 3 may suitably have a diameter of around 1.2 m. Each electrode 5 may, for example, have dimensions of around 100 mm in an axial direction along the pipe and 32 mm in a circumferential direction about the pipe.

The measurement system 1 further comprises a current source 6, a voltage monitor 7 and a controller 8. The controller 8 may be a programmable logic controller (PLC), such as, for example, a PLC manufactured by Bachmann electronic GmbH, Feldkirch, Austria. The controller 8 controls the current source 6 and the voltage monitor 7. The controller 8 also performs processing as described below in more detail.

The measurement system 1 also has a secondary sensor 9. The secondary sensor 9 may, for example, be a temperature sensor. The secondary sensor 9 is arranged to measure the temperature of the material 2 within the pipe 3. Alternatively, the secondary sensor 9 may be arranged to measure the temperature of the material 2 prior to being drawn into the pipe 3.

The measurement system 1 also has a gas fraction probe 10. The gas fraction probe 10 may, for example be an ultrasound probe. The gas fraction probe 10 is arranged to measure the volume of gas (e.g. air) entrained within the material 2 within the pipe 3. Gases, such as air, have a significantly higher attenuation of ultrasound than either liquids or solids (ultrasound attenuation being inversely proportional to density). Therefore, the attenuation of ultrasound by material provides an accurate measure of the proportion of gas, versus solid or liquid.

Figure 2:
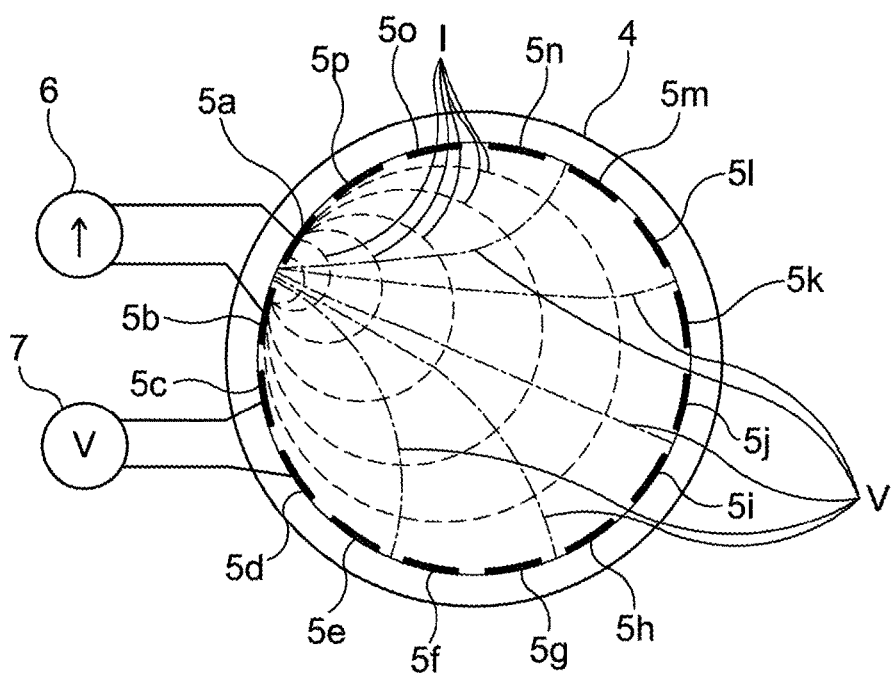
FIG. 2 shows a part of the measurement system shown in FIG. 1 in more detail.

FIG. 2 illustrates a cross-section through the sensor 4. The electrodes 5 are arranged circumferentially around the pipe 3. The electrodes 5 may be, for example, equally spaced around the internal surface of the sensor 4. Each of the electrodes 5 is formed from a conductive material, allowing electrical contact to be made between the electrodes 5 and the material 2 within the sensor 4 (and thus within the pipe 3). The electrodes 5 may be made from an erosion resistant material, such as, for example, stainless steel. The internal surface of the sensor 4 which is not covered by the electrodes 5 is formed from an erosion resistant material. For example the internal surface may be formed from a cast rubber or polyurethane material. Alternatively, the internal surface of the sensor 4 may be covered with replaceable ceramic tiles.

Each of the electrodes 5 is switchably connected to the current source 6. In the arrangement of FIG. 2, a first energisation electrode 5a and a second energisation electrode 5b of the electrodes 5 are connected to the current source 6. When connected, a circuit is formed by the current source 6, the first energisation electrode 5a, the material 2, and the second energisation electrode 5b. Current flows from the current source 6 into the material 2 via the first energisation electrode 5a, before returning to the current source 6, via the second energisation electrode 5b. The current source 6 supplies an alternating current (AC). The supplied current may, for example have a frequency of around 4.6 kHz. The use of an alternating current may reduce the occurrence of electrolysis at the electrodes 5.

Each of the electrodes 5 is also switchably connected to the voltage monitor 7. When connected to one of the electrodes 5 the voltage monitor is arranged to measure the electrical potential at that electrode. Each of the electrodes 5, being in electrical contact with the material 2, is at substantially the same potential as the material adjacent to each of the electrodes 5. Therefore, by measuring the electrical potential at the electrodes 5, the potential difference between different locations within the material 2 can be measured, as described in more detail below. The voltage monitor 7 may use synchronous techniques, such as, for example phase sensitive detection, to detect a signal having the same frequency as the current supplied by the current source 6. Such phase sensitive detection can provide enhanced noise immunity to wideband noise sources, by allowing detection only at the frequency supplied by the current source 6. The voltage monitor 7 may be configured to measure the magnitude of the signal received at the supply frequency. The voltage monitor 7 may also be configured to measure the phase angle of a measured signal with respect to the phase of any injected signal.

In the arrangement of FIG. 2, a first monitor electrode 5c and a second monitor electrode 5d of the electrodes 5 are connected to the voltage monitor 7. In this arrangement, the voltage monitor 7 is able to measure the potential difference between the monitor electrodes 5c and 5d, and thereby the potential difference between the regions of material 2 adjacent to the respective monitor electrodes 5c and 5d. The current flow and potential difference distribution within the material 2 is described in more detail below.

Figure 3:
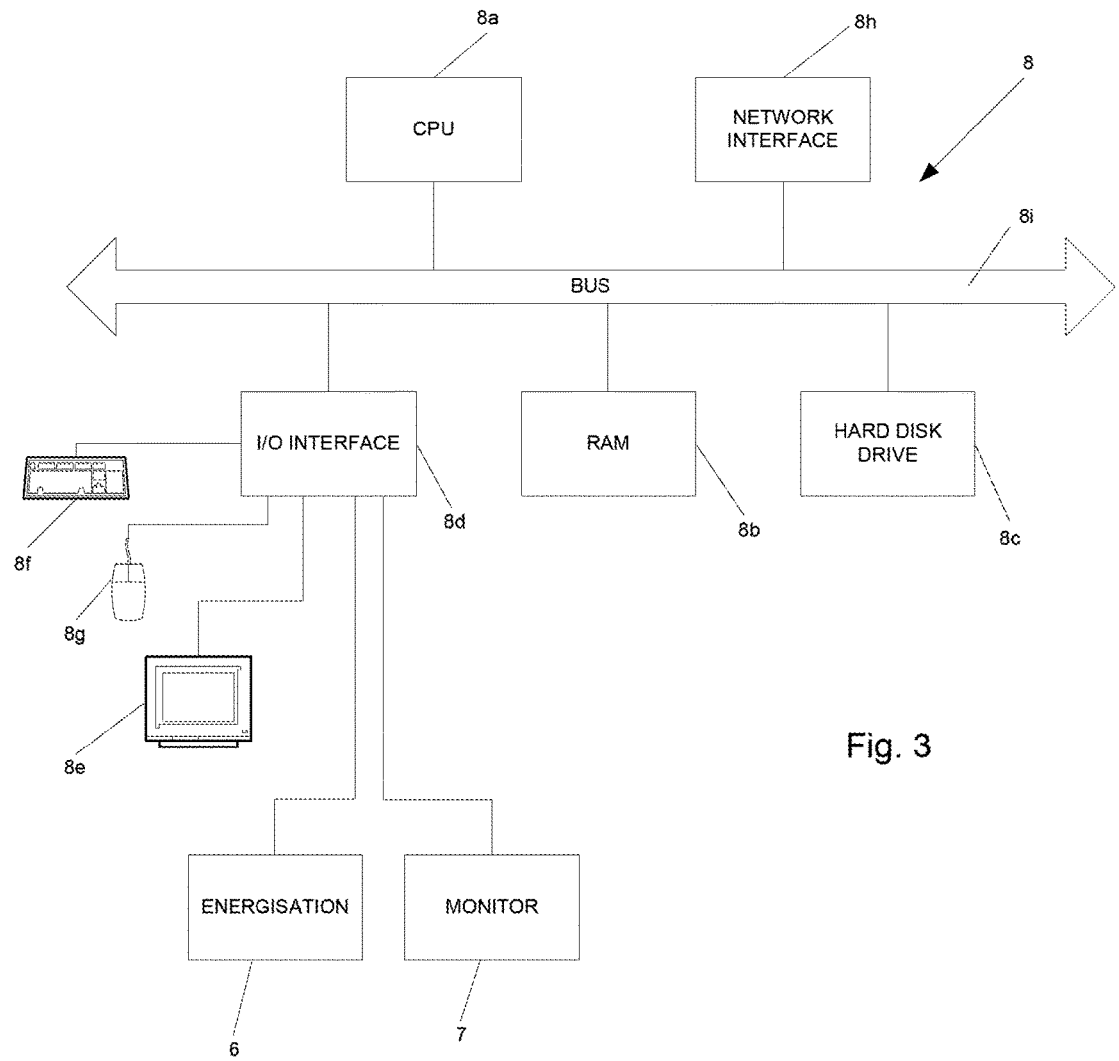
FIG. 3 shows a part of the measurement system shown in FIG. 1 in more detail.

FIG. 3 shows the controller 8 in further detail. It can be seen that the controller 8 comprises a CPU 8a which is configured to read and execute instructions stored in a volatile memory 8b which takes the form of a random access memory. The volatile memory 8b stores instructions for execution by the CPU 8a and data used by those instructions. For example, in use, measured potential difference values may be stored in the volatile memory 8b. The controller 8 further comprises non-volatile storage in the form of a solid state drive 8c. The measured potential difference values may be stored on the solid state drive 8c.

The controller 8 further comprises an I/O interface 8d to which are connected peripheral devices used in connection with operation of the controller, and with obtaining the measured potential difference values. More particularly, a display 8e is configured so as to display output from the controller 8. The display 8e may, for example, display a representation of the measured potential difference values, or a graphical user interface. Additionally, the display 8e may display images generated by processing of the measured potential difference values. Input devices are also connected to the I/O interface 8d. Such input devices include a keyboard 8f and a mouse 8g which allow user interaction with the controller 8. The current source 6 and voltage monitor 7 are also connected to the I/O interface 8d, allowing the controller 8 to control the current source 6 and the voltage monitor 7.

A network interface 8h allows the controller 8 to be connected to an appropriate computer network so as to receive and transmit data from and to other computing devices. For example, the controller 8 may be remotely controlled by a remote computer via the Internet. The CPU 8a, volatile memory 8b, solid state drive 8c, I/O interface 8d, and network interface 8h, are connected together by a bus 8i.

In use, the measurement apparatus 1 is controlled by the controller 8 to perform tomographic measurements on the material contained within the region of the pipe 3 surrounded by the EIT sensor 4. Tomography refers to the use of some form of penetrating wave to deduce properties of a region of interest. Generally, in tomography, an image is constructed by the combination of a plurality of image sub-regions, or pixels. Tomography can be applied to industrial processes, for example by imaging the contents of pipes within the industrial process. Such tomographic imaging enables parameters, such as conductivity, to be deduced relating to the contents of the process pipes. Thus, in combination with specific knowledge of the nature of the materials within a pipe, and with additional sensor information, accurate density measurements can be derived by using tomographic imaging.

In electrical impedance tomography (EIT) the penetrating waves are generated by the injection of electrical signals into the region of interest. Electrodes placed around the region of interest monitor the impedance of the material within the region of interest, by virtue of the potential differences caused by the injection of electrical signals. EIT can thus be used to distinguish between materials having different electrical resistivities or impedances within the region of interest. The following method may be used to monitor complex impedance (i.e. operating as electrical impedance tomography: EIT). Potential differences within the material, which are caused by the flow of injected current, are monitored. Both the magnitude and the phase (i.e. both the real and imaginary parts) of the monitored signals are used.

Moreover, in some parts of the following description the term complex conductivity is used. It will be appreciated that complex conductivity is an inverse of the complex impedance. The complex conductivity is the sum of the simple (real) conductivity and an imaginary component. Where the terms complex conductivity and complex impedance are used herein, it will be appreciated that where appropriate an impedance value may be converted to a conductivity value, and vice versa. For example, while the term electrical impedance tomography is conventionally used, it will be appreciated that such a technique may generate images (tomograms) which in fact are representations of (complex) conductivity.

Figure 4:
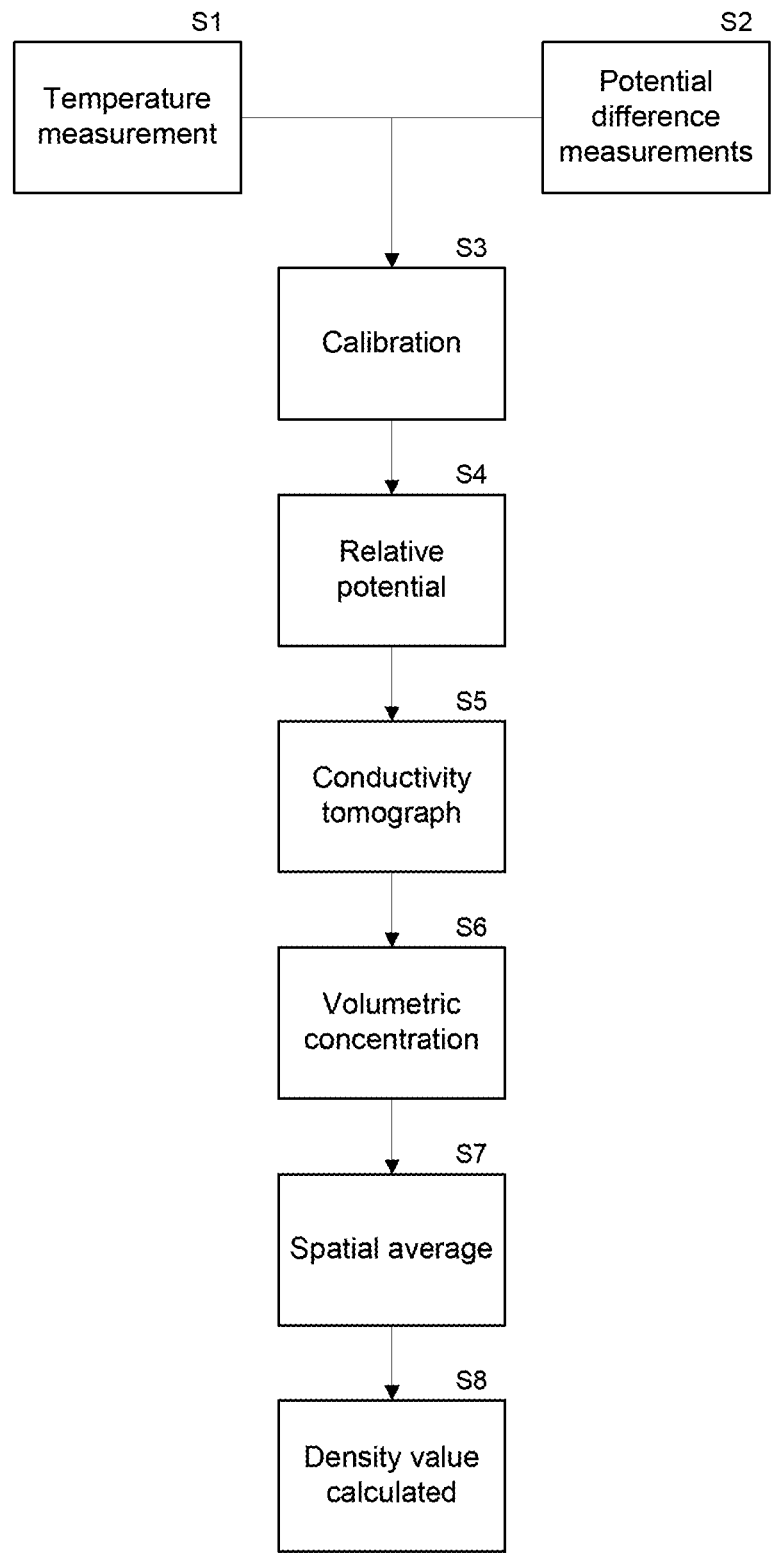
FIG. 4 shows a process carried out by the measurement system shown in FIG. 1.

FIG. 4 shows a process running on the controller 8. At steps S1 and S2 measurements are conducted to gather information related to the conductivity of the material 2 within the pipe. At step S1 a temperature measurement is made of the liquid component of material 2, allowing compensation for the known relationship between conductivity and temperature. At step S2, a series of potential difference measurements are conducted, providing relationships between current injected between pairs of the electrodes 5 and the potential difference, caused by that current injection, at different pairs of the electrodes 5.

Once this data has been collected, at step S3 a set of reference data is compensated for the temperature measured at step S1. The reference data provides a set of potential difference values which would be expected to be measured at the electrodes for a known energisation configuration and energisation level, given the presence of a reference material within the pipe 3 having a uniform conductivity distribution. This compensation forms part of a calibration process. The compensated calibration data is then compared the measured potential difference data at step S4, allowing differences between the measured and expected data to be determined. These differences are converted at step S5, by conventional tomographic techniques, to form a set of conductivity values for sub-regions of the material 2 within the pipe 3.

The generated conductivity values are then processed, at step S6, with the known conductivity values for each of the components within the material 2. For example, for a mixture of sand and saline water, reference conductivities for sand and saline water are used to calculate the proportion of sand and saline water which is present within each of the sub-regions. That is, the conductivity of the mixture of sand and saline water in each sub-region is effectively a weighted average of the conductivities of the two components, weighted based on their relative volume proportions. The weighting of that average (i.e. the relative volume proportions) can thus be calculated from the measured conductivity of the mixture, and the known conductivities of the two components.

The volume proportions (or volumetric concentrations) for each of the sub-regions are then averaged over the whole pipe 3 at step S7, to allow a single concentration value to represent the entire pipe cross-section. This concentration value is then converted at step S8, with reference to the known densities of the two components, to an average density value across the whole pipe 3.

Figure 5:
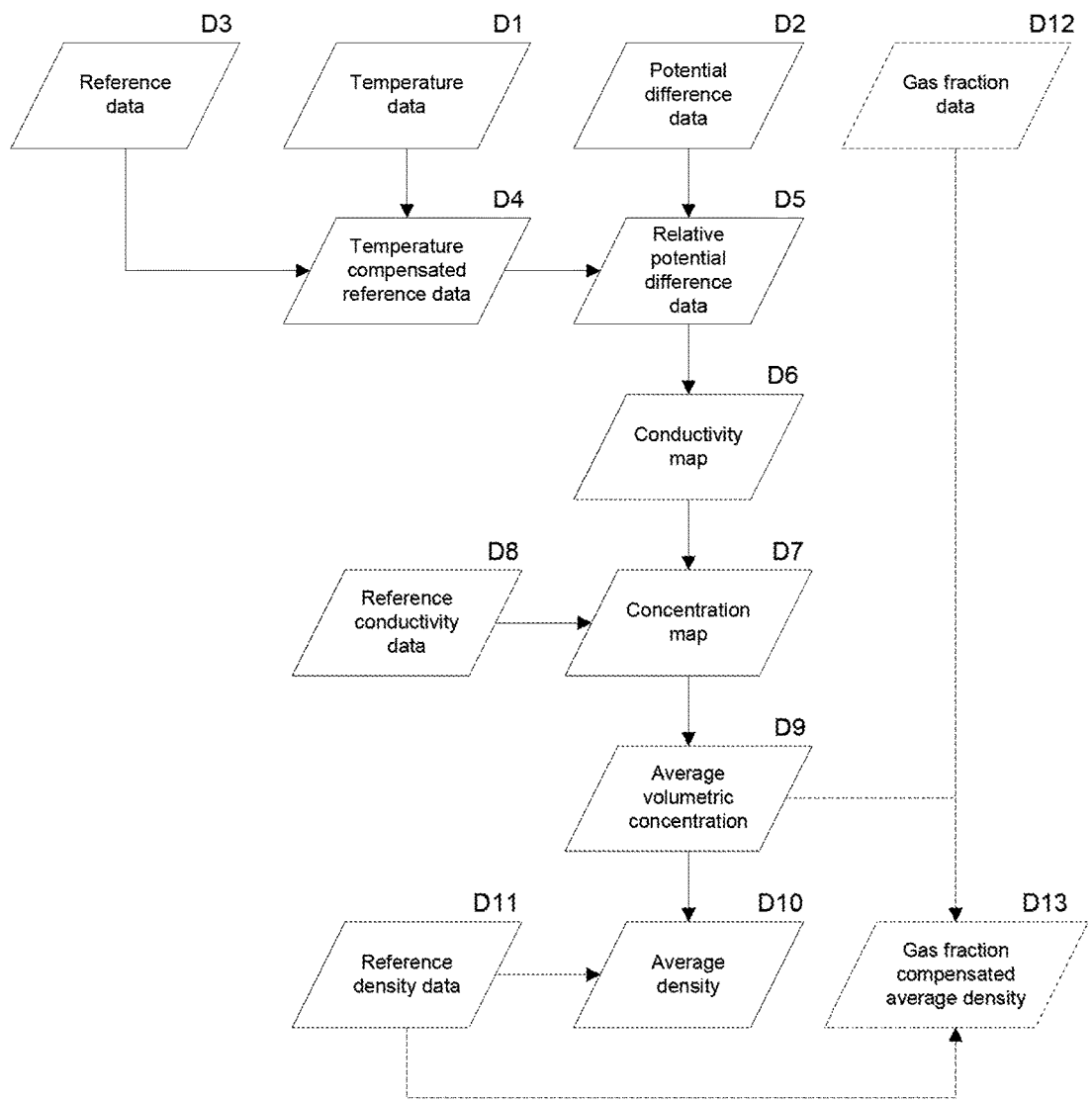
FIG. 5 shows data items processed by the measurement system shown in FIG. 1.

FIG. 5 shows the interaction between the various data items processed by the process running on the controller 8, as described above with reference to FIG. 4. Temperature data D1 and reference data D3 are combined to form temperature compensated reference data D4. This is further combined with measured potential difference data D2 to generate relative potential difference data D5. This relative potential difference data D5 provides improved accuracy when compared to measured potential difference data in that artefacts of the measurement apparatus and electrode configuration are removed.

Further processing converts the relative potential difference data D5 to a conductivity map D6, which describes the conductivity at each of the sub-regions within the pipe 3. This conductivity map D6 is combined with reference conductivity data D8 in order to generate a concentration map D7. That is, by making reference to the known conductivity the components of the material 2, it is possible to calculate the concentration of each of the components within the material 2, provided the conductivity of the material is known. A spatial average of the concentration map D7 is used to generate a single value which represented the average volumetric concentration D9 within the whole pipe 3.

Finally, this average volumetric concentration D9 can be used, in combination with reference density data D11, to calculate an average density D10 for the material 2 within the pipe 3. In addition, gas fraction data D12, which represents the proportion of the material 2 which is gas, can be combined with the average volumetric concentration D9 and the reference density data D11 to generate a gas fraction compensated average density D13. The gas fraction compensated average density D13 is an improved estimate of the average density D10, which is particularly beneficial where there are large proportions of entrained gas (e.g. air) within the material 2.

In more detail, at step S1 the secondary sensor 9 gathers data D1 relating to the temperature of the material 2 within the pipe 3. The conductivity of the material 2 within the pipe 3 may be strongly dependant on the temperature of the material 2. For example, a temperature change of 6 degrees Celsius may result in a conductivity change of 10% of saline water Concurrently with step S1, the controller 8 controls the sensor 4 to perform step S2. At step S2, the current source 5 is controlled to apply signals to the electrodes 5, while the voltage monitor 6 is controlled to measure potential differences at the electrodes 5. The measured potential differences provide the potential difference data D2. As described with reference to FIG. 2 above, the application of a current between first and second energisation electrodes 5a, 5b, causes a potential difference distribution within the material 2. When a current is flowing between the energisation electrodes 5a, 5b, a plurality of current paths exist between the electrodes. The current density is greatest closest to the electrodes 5a, 5b, however, current will flow throughout the material 2, albeit with a reduced current density. Dashed lines I indicate several current paths within the material 2, in response to the application of energisation to the electrodes 5a, 5b.

The flow of current throughout the material 2 causes a corresponding potential difference distribution throughout the material 2, current flowing from a higher potential to a lower potential. This potential difference distribution can be understood with reference to dash-dot lines V, which represent lines of isopotential within the material 2. That is, all points on each of the lines V have the same electrical potential as each of the other points on the same line V (and a different potential to all points on each of the other lines V). The electrical potential within the material 2 gradually decreases from a highest value immediately adjacent to the first energisation electrode 5a, to a lowest value immediately adjacent to the second energisation electrode 5b. While it is not possible to directly measure the potential at all points within the material 2, the above illustrated potential difference distribution allows measurements conducted between electrodes which are distant from the energisation electrodes to provide information regarding the potential difference distribution. Moreover, non-uniformities in the conductivity of the material 2 cause disturbances to the potential difference distribution, which disturbances can be monitored by their effect on the potential difference values measured at the electrodes 5. It can be seen, therefore, that by measuring the magnitude of the potential difference between electrodes 5c and 5d, information relating to the potential difference distribution within the material 2 can be gathered. Similarly, by measuring the magnitude of the potential difference between the electrodes 5d and 5e, further information relating to the potential difference distribution within the material 2 can be gathered. This process can be repeated for each of the adjacent pairs of electrodes which are not energisation electrodes (i.e. 5c-5d, 5d-5e, 5e-5f, . . . , 5o-5p). Where there are 16 electrodes, this results in 13 monitor electrode pair measurements for each energisation configuration. Thus, while the electrodes 5c and 5d are illustrated as monitor electrodes in FIG. 2, by measuring the potential difference between each of the adjacent pairs of the electrodes 5c-5p, a map of the potential difference within the material 2 when electrodes 5a and 5b are energisation electrodes can be created.

Once each of the pairs of monitor electrodes has been measured, as described above, the energisation configuration is switched such that a different pair of electrodes is the energisation electrodes. For example, the first and second energisation electrodes may be switched to become the electrodes 5b and 5c respectively. A current is applied, by the current source 6, between the electrodes 5b, 5c, as described above with reference to the electrodes 5a, 5b, and the electrical potential is measured by the voltage monitor 7 at each of the 13 adjacent pairs of monitor electrodes (5d-5e, 5e-5f, . . . , 5o-5a).

In the above described EIT sensor configuration, having 16 electrodes 5, there are 16 possible energisation electrode configurations, and 13 monitor electrodes configurations for each of those 16 energisation electrode configurations, resulting in 208 unique measurement configurations. However, while 208 unique measurement configurations exist, where a measurement configuration is a direct inverse of an earlier measurement configuration (e.g. where the energisation and monitor electrodes are simply reversed), the measurement configuration can be omitted, requiring 104 independent measurements to be taken for each density value calculation.

Following the collection of measurements at steps S1 and S2, at step S3 the controller 8 performs a calibration compensation. The calibration compensation is based upon the output of the secondary sensor 9 (i.e. temperature data D1), and calibration reference data D3. The calibration reference data D3 is stored within a memory of the controller 8, such as, for example, the solid-state disc 8c. The calibration reference data D3 provides a set of potential difference values which would be expected to be measured at the monitor electrodes for a known energisation configuration and energisation level, given the presence of a reference material within the pipe 3 having a uniform conductivity distribution. Thus, the calibration reference data D3 provides a reference level against which the measured potential difference data D2 can be compared. This comparison allows accurate conductivity values throughout the material 2 to be generated, based upon the measured potential difference data D2 and the reference data D3. The use of reference data allows the effect of measurement artefacts, such as, for example, those caused by electrode size and position, and electrode surface condition, to be reduced.

The calibration reference data D3 is collected by performing measurements on an EIT sensor having a similar electrode configuration and geometry to the EIT sensor 4. Further, the calibration reference data D3 is collected while a material having known solid and liquid component concentrations, densities and temperatures is within the EIT sensor. Thus the use of calibration reference data D3 minimises the effect of electrode configurations and device geometry, allowing any changes in the material 2 within the sensor 4 to be identified more accurately. Further, the use of a reference material which is similar to the material 2 within the sensor 4 allows any changes in the conductivity to be attributed to changes in concentration, rather than to changes in material properties.

For example, the reference material may comprise a liquid component having a known conductivity, such as, for example, saline water having a salinity and temperature which is similar to that of sea water. Alternatively, the reference material may comprise a mixture of a known proportion of a liquid component having a known conductivity and a known component of a solid component having a known conductivity. For example, the reference material may comprise a mixture of sand and saline water in the volume ratio 1:9, the saline water having a salinity and temperature which is similar to that of sea water.

It will be appreciated that reference materials may be selected in dependence upon the intended application of the density measurement apparatus. It will further be appreciated that the closer a reference material resembles the material 2, the better the accuracy of any measured density value.

Before any comparison is made between the reference data D3 and the measured potential difference data D2, the calibration reference data D3 is compensated to take into account the operational temperature of the material 2, generating temperature compensated reference data D4. This temperature compensated reference data D4 may be stored within a memory of the controller 8, such as, for example, the solid-state disc 8c.

Once this calibration compensation step is complete, processing passes to step S4, where the temperature compensated reference data D4, and the potential difference data D2 are processed. The relative difference between each of the temperature compensated reference data D4 values and the measured potential difference data D2 values is determined, and relative potential difference data D5 generated. The use of reference data and its comparison with measured data to generate relative potential data allows the effects of different material properties to be taken into account. The stored reference data D3 should thus relate to a mixture of components which have similar electrical properties to the material 2. It will be appreciated that several sets of reference data D2 can be stored, each relating to a different material.

Once the relative potential difference data D5 has been generated, processing passes to step S5. At step S5 the relative potential difference data D5 is processed by the CPU 8a to generate a set of conductivity values D6. Known algorithms exist for converting individual potential measurements to a two-dimensional map of the electrical conductivity (or resistivity). These algorithms can be applied by the controller 8 to generate the two-dimensional map of the electrical conductivity of the material 2 within the pipe 3. The generated two-dimensional map comprises a plurality of conductivity values D6, each of which is associated with a sub-region within the sensor 4. The region within the sensor 4 may suitably be divided into 316 sub-regions.

Each sub-region has an equal area in the plane of the sensor 4, that area being a fraction of the area of the cross-section of the sensor 4. The dimension of the electrodes 5 along the length of the pipe 3 determines the effective depth of each of the sub-regions. Therefore, the conductivity value associated with each sub-region is an average conductivity across the depth of the sub-region (and thus the depth of the sensor electrodes 5). It will be appreciated that fringing effects can result in material immediately adjacent to each of the sub-regions influencing the flow of current within the sub-regions; however, this effect is considered to have a negligible impact on the measured conductivity.

Once the conductivity values D6 have been generated at step S5, processing passes to step S6. At step S6 the each of the conductivity values D6 is converted to a volumetric concentration D7. The volumetric concentration D7 in each sub-region provides a measure of the volume proportion of the solid component within the material 2 within each of the sub-regions. A volumetric concentration value of '0' equates to no solid (i.e. only liquid), while a volumetric concentration value of '1' equates to no liquid (i.e. only solid) being present. The volumetric concentration D7 in each sub-region is calculated according to the Bruggeman equation:

$$C_{vol} = 1 - \left[ \frac{(\sigma_{mc} - \sigma_2)}{(\sigma_1 - \sigma_2)} \times \left( \frac{\sigma_1}{\sigma_{mc}} \right)^{1/3} \right] \quad (1)$$

where:
- $C_{vol}$ is the volumetric concentration D7 of solid material within the sub-region;
- $\sigma_{mc}$ is the (temperature compensated) conductivity value D6 of the material within the sub-region;
- $\sigma_1$ is the (temperature compensated) conductivity of the liquid component; and
- $\sigma_2$ is the conductivity of the solid component.

The conductivities $\sigma_1$, $\sigma_2$ of the liquid component and solid component form reference conductivity data D8.

Processing then passes to step S7, where a spatial average is taken over all of the sub-regions, generating an average volumetric concentration D9 ($C_{vol,mean}$). The average volumetric concentration D9 is calculated as the arithmetic mean of each of the volumetric concentration values D7. The average volumetric concentration D9 is a measure of the average volumetric concentration of solid within the material 2 within the entire pipe 3 at the location of the EIT sensor 4.

Once the average volumetric concentration D9 has been generated at step S7, processing passes to step S8. At step S8 the average density D10, or specific gravity, is calculated from the average volumetric concentration D9. The average density D10 is calculated according to the following formula:

$$\rho_{mixture} = [(C_{vol,mean}) \times (\rho_{solid} - \rho_{liquid})] + \rho_{liquid} \quad (2)$$

where:
- $\rho_{mixture}$ is the average density D10 of the material 2 within the region;
- $\rho_{solid}$ is the reference density of the solid component; and
- $\rho_{liquid}$ is the reference density of the liquid component.

The densities $\rho_{solid}$, $\rho_{liquid}$ of the solid component and liquid component form reference density data D11. The reference density data D11 may be compensated for the correct temperature of the mixture.

The output of the process described with reference to FIG. 4 is thus a single density value D10 for the entire volume of material 2 within the pipe 3, at the location of the EIT sensor 4 at the point in time the measurements were captured. This density value D10 is provided to process control equipment as an output from the controller 8 if required. As described above, in order to generate each density value D10, 104 measurements are taken. Each measurement may, for example, take around 25 ms to collect. Density values may, for example, be generated at around 0.4 Hz. It will be appreciated that density values can be generated at any required data rate. For example, if a particularly high data rate was required, several voltage measurements may be conducted in parallel.

Other outputs can also be generated as required. For example, the two-dimensional conductivity map (comprising conductivity values D6) can be exported as an output if required. Furthermore, the processing described at step S6, or steps S6 and S8 (omitting the averaging step at step S7) may be carried out prior to generating an output map, allowing a two-dimensional volumetric concentration map, or a two-dimensional density map to be generated as required. Such two-dimensional maps may be referred to as tomograms.

In addition to the processing described above with reference to FIG. 4, in some embodiments further measurements and processing steps may be carried out in order to achieve improved accuracy. For example, measurements taken by the gas fraction sensor 10 allow a density calculation to be carried out with improved accuracy where entrained gas (or air) is present within the material 2.

In one such embodiment, additional gas fraction data D12 is collected, for example at step S1. The gas fraction data D12 is combined with the average volumetric concentration D9, in order to provide a gas fraction compensated average density D13 ($\rho_{mixture}$), in a modified step S8, according to modified equation:

$$\rho_{mixture,no\_gas} = [(C_{vol,mean} - C_{vol,gas}) \times (\rho_{solid} - \rho_{liquid})] + \rho_{liquid} \quad (3)$$

where:
- $\rho_{mixture,no\_gas}$ is the gas fraction compensated density D13 of the fluid within the region (i.e. compensated for any gas present); and
- $C_{vol,gas}$ is the gas fraction data D12 (i.e. the volume proportion of any entrained gas within the material, as measured by the gas fraction probe 10).

The gas fraction compensated density D13 thus allows compensation for entrained gas within the mixture. Where no such compensation is made, and where there is a significant proportion of entrained air, the average volumetric concentration D9 may interpret regions of air (low conductivity) as solid, rather than liquid. As such, any resulting average density D10 may be artificially high, unless compensated for gas volume.

In addition to the processing described above with reference to FIG. 4, in some embodiments further measurements and processing steps may be carried out in order to achieve improved accuracy. For example, while the above described method makes use only of the magnitude of the potential difference measured at the monitor electrodes, the phase of the potential difference may also be used to deduce additional information about the material 2. Such processing may be carried out in addition to, or instead of, any gas fraction compensation.

Large particulates, such as, for example, particles of sand, respond quite differently to AC currents than small particulates, such as, for example particles of clay. Large particulates typically exhibit a simple resistance (i.e. no imaginary part to impedance). Small particulates, on the other hand, typically exhibit a complex impedance (i.e. both real and imaginary parts) due to their large surface are to volume ratio, and related surface charge effects. Therefore, both the phase and magnitude of the monitored potential difference are measured, and this information used to determine an improved estimate of the total proportion of large particulates (e.g. sand) and small particulates (e.g. clay) within a mixture. Large particles may, for example, be considered to be particles having a minimum dimension of greater than about 50 µm, such as for example about 100 µm. Small particles may, for example, be considered to be particles having a minimum dimension of less than about 1 µm, such as for example about 100 nm.

An AC current is injected to the material 2 between energisation electrodes, as described above with reference to FIG. 2. Signals are then measured at each of the monitor electrodes. The measured signals are then processed, as described above with reference to FIG. 4 to generate a map of impedance values. However, rather than each sub-region having a simple conductivity (or resistance) value, each sub-region is provided with a complex impedance value, having both real and imaginary parts, based on both magnitude and phase of the measured voltages. Any real component is considered to be related to the presence of both large particulates and small particulates, whereas any imaginary component is considered to be primarily related to the presence of small particulates. Therefore, if only the real component of the impedance is used, sensitivity to small particulates may be reduced. Similarly, if only the imaginary component of the impedance is used, sensitivity to large particulates may be reduced. However, it is possible to achieve an improved estimate of the total volume fraction, using a modified equation based upon equation (1) above:

$$C_{vol} = 1 - \left[\frac{(K_{mc} - \sigma_2)}{(\sigma_1 - \sigma_2)} \times \left(\frac{\sigma_1}{K_{mc}}\right)^{1/3}\right], \quad (4a)$$

$$K^*_{mc} = \sigma'_{mc} + i\sigma''_{mc}, \quad (4b)$$

$$K_{mc} = |K^*_{mc}| = \sqrt{(\sigma'_{mc})^2 + (\sigma''_{mc})^2}, \quad (4c)$$

where:
$K^*_{mc}$ is the complex conductivity presented by large and fine particles,
$K_{mc}$ is the modulus of $K^*_{mc}$,
$\sigma'_{mc}$ is the real part of the complex conductivity; and
$\sigma''_{mc}$ is the imaginary part of the complex conductivity;

More generally, where it is known that a solid component of a mixture has a substantially homogenous density and size distribution, and a large particulate size, a single apparent density can be used in the calculations described above based upon real impedance data. However, where a small particulate is present imaginary impedance can provide useful additional information. Furthermore, where a mixture of small and large particulates is known to be present, both real and imaginary impedance values are used to derive information relating the total large and small particulate fractions. Moreover, where only small particulates are present imaginary impedance (and imaginary conductivity) can be used in equation 1 to determine the volumetric concentration of the small particulates within the material.

The differences between real and imaginary impedance components of different sized particles can be understood by reference to such particles' relative surface area to volume ratios at the same particle volumetric concentration. The surface area to volume ratio is inversely proportional to the dimension of particle (e.g. the diameter for a spherical shape). A small particle having a large surface area to volume ratio can carry proportionally more surface charge than a large particle, which has a small surface area to volume ratio. An applied electric field causes current to flow within the material. Any surface charge carried by particles within the material interacts with the current flow. Large particles are not significantly influenced by any interaction between their surface charge and the current flow, as their small surface area to volume ratio results in a relatively small ability to carry surface charge. Small particles, on the other hand, which have a relatively large surface area to volume ratio, and thus ability to carry surface charge, may be significantly influenced by the flow of current within the material, causing a phase lag in any monitored electrical parameter.

A material containing primarily large or small particulates, or a mixture of both, can be characterised by use of a reference material (and associated reference data) which has a similar mixtures of large and small particulates—and thus generates reference data having an appropriate combination of real and imaginary components).

Further still, where a mixture having several different solid components is present, each of which may have a different density (e.g. silica having a density of around 2.62 g/cm³, whereas iron oxide has a density of around 5.2 g/cm³ or greater), an assumption should be made as to the relative proportions of each component, so as to provide an accurate input to equations (1) and (3) above.

In the above described embodiments, an EIT sensor having 16 electrodes is described. However, EIT sensors having different numbers of electrodes can also be used. A sensor may have any arbitrary numbers of electrodes. Furthermore, while a simple ring of electrodes is described above, electrodes may be arranged in any convenient pattern. The electrode pattern may be varied in dependence upon the geometry of the vessel within which it is to be used. Moreover, while pipes having a circular cross-section are described above, vessels having non-circular, and irregular cross-sections are also envisioned. Where an energisation is applied between a first pair of electrodes, and an electrical parameter is monitored between a second pair of electrodes, a sensor having at least 4 electrodes should be provided. In order to improve the accuracy of the measurement process, a greater number of electrodes are generally provided. For example, a sensor having at least 8 electrodes would provide significantly higher resolution tomographic imaging than a sensor having 4 electrodes. Further, a sensor having 16 electrodes would provide significantly higher resolution tomographic imaging than a sensor having 4 or 8 electrodes. It will be appreciated that additional electrodes can be added to increase resolution.

In the processing described above, a regular distribution of sub-regions is provided within the region to be imaged. However, in some embodiments, an irregular distribution of sub-regions may be preferred. For example, for regions which are known to have a high solid concentration variability a higher sub-region resolution may be used than regions which are known to have a consistent solid concentration. In such an embodiment, any mean volumetric concentration should be adjusted so as to provide an accurate average (e.g. by calculating a weighted mean).

The measurement protocol described above requires the injection of current between pairs of adjacent electrodes, and the measurement of potential differences between pairs of the adjacent remaining electrodes. However, other measurement protocols may be used as required. For example, current may be injected, and/or potential differences measured between opposite electrodes.

The secondary sensor is described above as being temperature sensor. However the secondary sensor may be any form of sensor which allows for conductivity compensation. For example, the secondary sensor may be a simple conductivity sensor arranged to measure the conductivity of one component of the mixed material prior to mixing, or at the waste stream from a pump (i.e. where solids have been removed by filtration). Alternatively, a conductivity sensor may measure the liquid conductivity in a by-pass pipe, or in a gravitational separation pipe, allowing any solid particulates to be removed prior to conductivity measurements being conducted.

Additionally, the use of a secondary sensor is optional. In some applications environmental conditions may be sufficiently stable, and/or sufficiently well known, that further temperature and/or conductivity measurements are not required to perform calibration compensation. Similarly, the calibration compensation step itself can be omitted in some scenarios. For example, where the reference data is considered to be representative of the measurement conditions no calibration compensation is required.

The system described herein is described as having a current source 6 and voltage monitor 7. The current source 6 is an example of an energisation source. The voltage monitor 7 is an example of a monitor. However, it will be appreciated that any suitable form of energisation source may be used in combination with any suitable form of monitor. The energisation source may be any source which is capable of generating and injecting a suitable signal into the material 2. For example, the energisation source may be a voltage source, the current supplied by which is monitored during measurements.

Energisations and measurements are generally described as being applied to, and taken between, pairs of electrodes. However, it will be appreciated that energisations and measurements may be made with reference to a common reference electrode, or a plurality of electrodes. Furthermore, while sequential measurements are described, multiple measurements may be carried out in parallel. Where a common reference electrode is used, as few as three electrodes may be used.

The method described above generates a single measurement which represents the density of material within the pipe 3 at a single moment in time. However, in order to improve the accuracy of this measurement, several measurements may be taken, and a temporal average calculated. The use of a temporal average allows the effect of fluctuations such as those caused by turbulent flow, to be reduced. Any convenient number of samples may be averaged as required.

Furthermore, depending on the material flow rate within the pipe, it may be possible to estimate the mass flow rate, or solids flux, by combining density measurements with data indicative of the flow rate. By integrating over several such measurements, it is possible to estimate the total mass of a solid component which has been transported in a predetermined time period.

That is, rather than simply generating data indicative of the static density of material in a region of the pipe at any given time, the techniques described here can be applied so as to determine the solids flux, or mass flow rate per unit area of a pipe, enabling effective monitoring and control of an industrial system.

In addition to applications in dredging, embodiments of the invention may be used to measure the density liquid/solid mixtures in other industrial applications. For example, a density measurement apparatus may be used within a minerals processing plant. In such an apparatus a pipe and associated EIT sensor may have a diameter appropriate for the particular process. For example, the pipe and sensor diameter may be between 100 and 300 mm. Electrode dimensions are adjusted to accommodate a reduced sensor diameter. Within a minerals processing plant, knowledge of mass flow between various process stages provides important process control information. As such, accurate density measurements allow process throughput to be managed, for example by ensuring a critical mineral ore component is delivered at a required mass flow rate. The supply of a component may, for example, be increased, or reduced, based upon the measured density, allowing a predetermined mass flow rate, or total mass, or the component to be delivered.

In an alternative example within a minerals processing plant, a particular process stage may concentrate a material via froth flotation. A particular metallic ore may be concentrated to form a froth product (i.e. a highly aerated slurry). A density measurement apparatus can provide accurate concentration measurements of the mineral component within the froth product, allowing important information to be gathered relating to the efficacy of the froth flotation process. It will be appreciated that where a mineral refinement process is operated, any solid component within a flotation froth is likely to be a single mineral species (e.g. a particular metallic ore), thus allowing a single density value representative of that mineral to be used in the calculations described above.

While embodiments of the invention are described above as being used to generate data indicative of the slurry density of a material within a region of interest, it will be appreciated that such data may be an accurate representation of the slurry density, or, alternatively, be an estimate of the slurry density. In particular, while, in some application environments accurate data relating the densities of constituent materials within the slurry, and the state of dispersion of such constituent materials, may be available, in other environments such data may not be available. It will be appreciated, therefore, that the techniques described herein can be used to generate an estimate of the slurry density which is based upon various estimates and assumptions which are considered to be representative of a particular quantity (e.g. constituent material density).

For example, while the densities $\rho_{solid}$, $\rho_{liquid}$ of solid and liquid components as provided in equation (2) above may be accurate representations of the relevant quantities, they may also be estimates. Further, while it may be assumed that a particular solid component is equally distributed within a slurry, it may also be distributed in an uneven way, for example due to aggregation or flocculation. Such an uneven distribution may result in a calculated density value being suitable only as an estimate, rather than being an accurate representation of the actual slurry density.

Thus, while to generate accurate density values accurate component densities, conductivities, and distribution information may be required, in some cases where such accuracy of input data is not available, estimates of density can be generated. Moreover, by comparing estimates generated from different slurry samples, or at different times, a relative density, or change in density can be generated which provides useful process information.

It will be understood that where a region of interest (e.g. a pipe) is partially filled with a slurry, additional challenges may be faced when trying to determine a measure of slurry density. For example, conductivity values for solids and gaseous regions may be similar, resulting in difficulty in distinguishing between regions of gas and solid. Further, where an interface region is formed between a slurry and a gas, this interface may comprise a mixture of phases (e.g. a froth) and any analysis of conductivity values of such a region may indicate an erroneous density—for example as a result of similar conductivity values for gas and solid.

Figure 6:
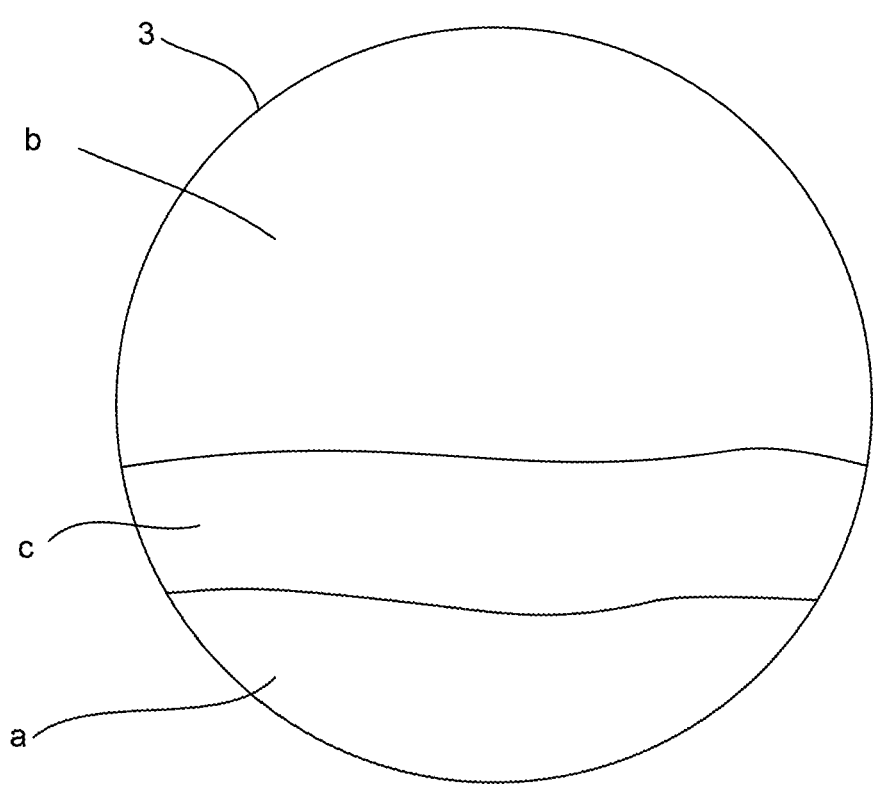
FIG. 6 shows a schematic illustration of a reference flow pattern for use in processing carried out by a measurement system as shown in FIG. 1 so as to perform an alternative embodiment of the invention.

Such challenges may be particularly relevant in systems such as gravity fed conveying systems in which slurry passes along a substantially horizontal pipe. FIG. 6 illustrates schematically a cross-section of the flow within such a pipe. A first flow region 'a' within the flow primarily consists of a slurry (that is solid particulates suspended in a liquid). A second flow region 'b' primarily consists of a gas (e.g. air). A third flow region 'c' is present between the first and second regions, and consists of a mixture of solid, liquid and gas. The flow region c may comprise a foam or froth, and/or may be referred to a supernatant region or interface region.

FIGS. 7a and 7b show representations of conductivity data collected from a pipe by an EIT sensor using techniques described above. The region within the pipe is represented by 316 sub-regions, or pixels, with each sub-region having a single numerical value associated with it. The same data is represented in both FIGS. 7a and 7b, with each sub-region of FIG. 7a being shaded according to the data value, while FIG. 7b shows just the data value. The numerical value may, for example, be a conductivity value for material within the relevant sub-region. It can be seen that there is a variation of conductivity data within the region.

A first flow region A of the image generally corresponds to a region of flow within the pipe which comprises a mixture of liquid and solid (i.e. a slurry). It should be noted that the image shown in FIG. 7 is rotated with respect to the orientation of the pipe from which the data was collected such that the lowest portion of the pipe is represented by the flow region A, which is to the upper-right hand portion of the image.

A second flow region B of the image occupies the lower-left hand portion of the image, and generally corresponds to a region of air within the pipe (i.e. with no solid concentration).

A third flow region C of the image occupies the boundary between the flow regions A and B, and can be seen to run from the upper left of the image to the lower-right hand side. This flow region C represents the interface where there is some gas, some liquid, and some solid within the liquid. While the boundaries of the flow regions A, B and C are difficult to define exactly, it will be appreciated that, in general terms at least, they can be considered equivalent to the flow regions a, b and c shown in FIG. 6.

Further, while the conductivity data associated with each of the sub-regions within the image (as shown in FIG. 7) can be derived from measurement taken by the EIT sensor 4, it will be appreciated that in some cases this does not allow accurate information regarding certain properties of the material within that pipe to be the generated. For example, where low conductivity can indicate either the presence of solid, or the presence of gas (e.g. air), it may be impossible to determine the volumetric concentration of solids, and thus the slurry density directly from the conductivity data. As such, techniques have been developed to identify the various flow regions A, B, C as described above, and to generate concentration data based upon information indicative of the flow regions A, B and C in combination with the conductivity data.

For example, by identifying sub-regions which fall within the flow region B (i.e. air) the apparent concentration of solids in that sub-region can be disregarded as being false. Further, by identifying sub-regions which fall within the flow region C (i.e. interface) the apparent concentration of solids in that sub-region can be scaled by a value which is considered to represent a more accurate measure of the concentration of solids in that region. Finally, by identifying sub-regions which fall within the flow region A (i.e. slurry) the apparent concentration of solids in that sub-region can be treated as being an accurate representation of the concentration of solids in that sub-region.

Figure 8A:
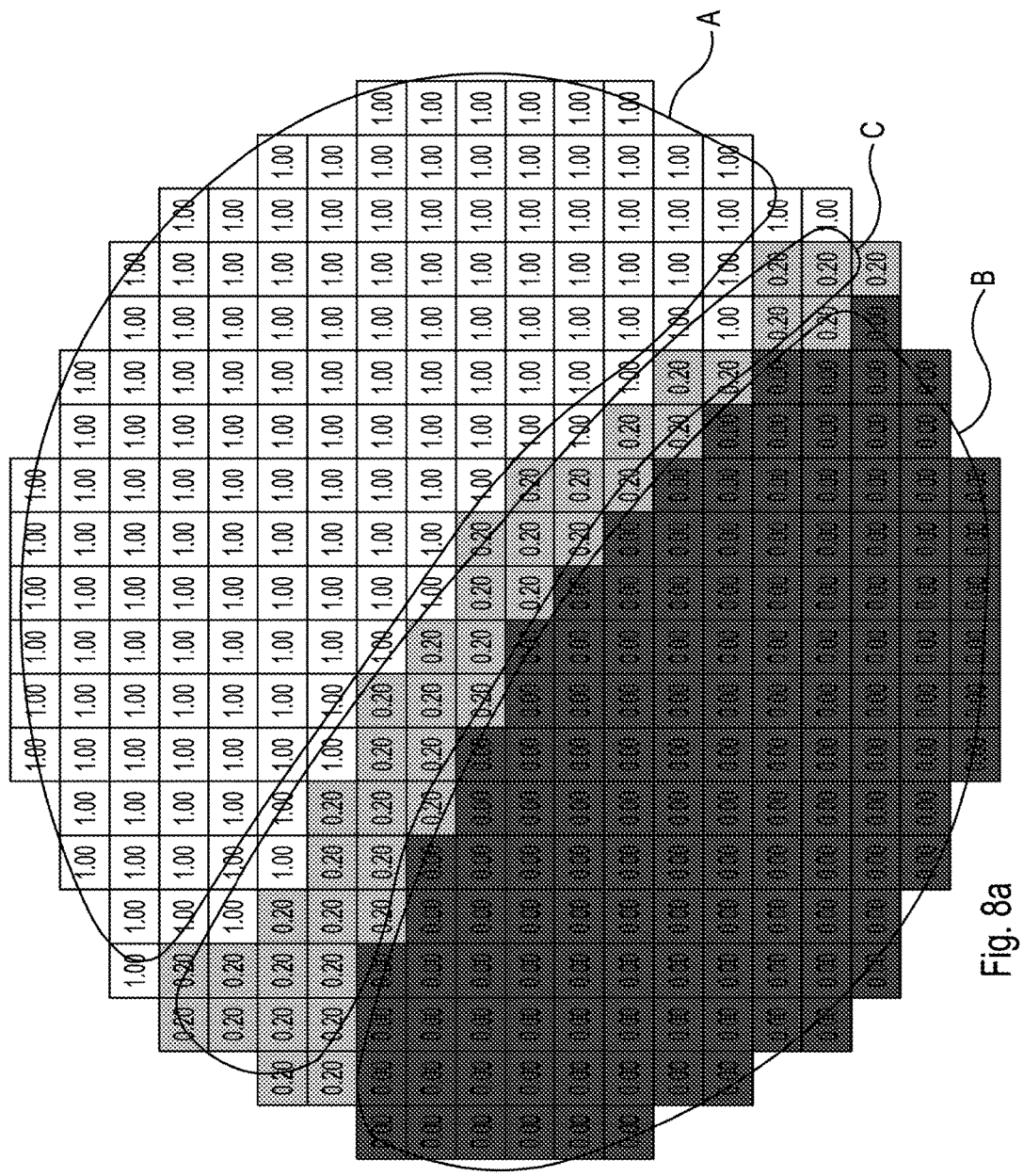
Figure 8B:
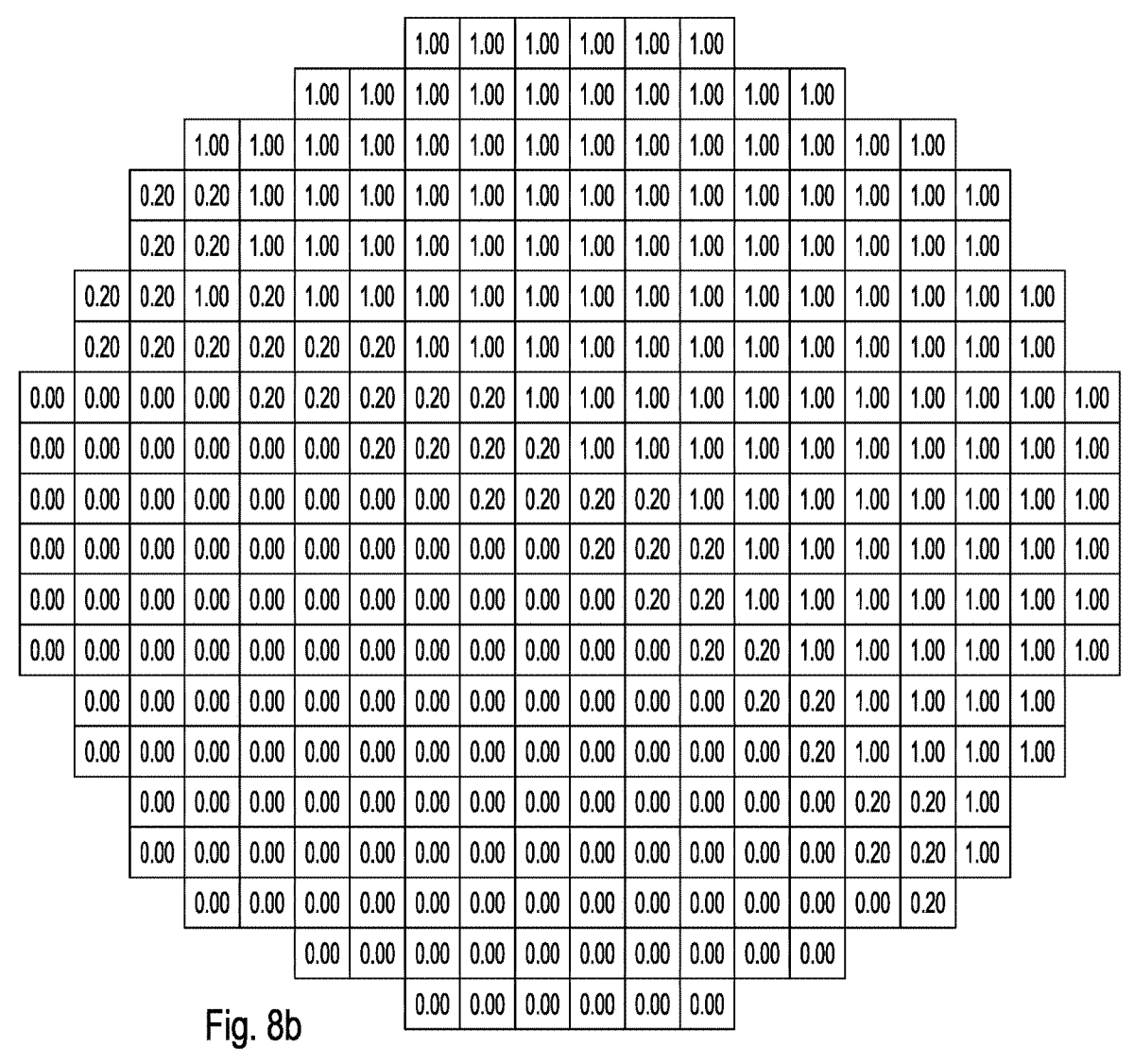

FIGS. 8a and 8b show a mask which is generated based upon the data shown in FIGS. 7a and 7b. In the mask of FIGS. 8a, 8b sub-regions are each assigned a value 0, 0.2 or 1. The same data is represented in both FIGS. 8a and 8b, with each sub-region of FIG. 8a being shaded according to the data value, while FIG. 8b shows just the data value. Sub-regions which are identified as belonging to the flow region A, are assigned a value 1. Data associated with those sub-regions will scaled by the factor 1, and is thus treated as being an accurate representation of the concentration of solids in that sub-region.

Sub-regions which are identified as belonging to the flow region B, are assigned a value 0. Data associated with those sub-regions will be scaled by the factor 0, and is thus treated as not being an accurate representation of the concentration of solids in that sub-region.

Sub-regions which are identified as belonging to the flow region C, are assigned a value 0.2. Data associated with those sub-regions will scaled by the factor 0.2, and is thus treated as being an over-representation of the true concentration of solids in that sub-region, and scaled accordingly.

FIGS. 9a and 9b shows a representation of the data represented by FIGS. 7a and 7b, having been scaled by the mask of FIG. 8a, 8b. The same data is represented in both FIGS. 9a and 9b, with each sub-region of FIG. 9a being shaded according to the data value, while FIG. 9b shows just the data value. Each of the 316 sub-regions now has a single numerical value associated with it which is based upon the data of FIG. 7a, 7b, but multiplied by 0, 0.2 or 1, depending upon whether it is classified as being in flow region A, B or C.

Once the data associated with each of the sub-regions has been appropriately scaled (or effectively excluded by virtue of a zero scaling factor), an effective average concentration can be derived. That is, by taking a numerical average of each of the non-zero conductivity values, a value which is representative of the average conductivity of the material within flow regions A and C can be derived. Where there is a well-known relationship between the conductivity and the volumetric concentration of solids within the liquid (as discussed in more detail above), the average conductivity value can be considered to be indicative of the volumetric concentration of solids within the flow regions A and C.

Moreover, with knowledge of the number of non-zero sub-regions (i.e. the number of sub-regions within the flow regions A and C), the average conductivity can be scaled so as to be representative of average volumetric concentration of solids within the whole pipe.

The processing described above with reference to FIGS. 6 to 9 is now described in more detail with reference to FIG. 10, which shows a process running on the controller 8.

Processing starts at step S10 where conductivity data related to the conductivity of the material 2 within the pipe is obtained. The obtained data takes the form of a set of conductivity values each being associated with a sub-region within the pipe, for example, as shown in FIGS. 7a, 7b.

Processing then passes to step S11 where the obtained data is processed so as to generate horizontal and vertical profiles. A horizontal profile may be generated by generating a numerical average of each column of data within the obtain data.

FIG. 11a shows an exemplary intensity plot (based upon a different set of data from FIGS. 7 to 9) showing the conductivity at various regions within a pipe. FIG. 11b shows a plot of a horizontal profile based upon the data of FIG. 11a. The vertical axis shows the average intensity (not to scale) at each horizontal location across the pipe (horizontal axis). In the illustrated plot it can be seen that the conductivity profile peaks slightly to the right of the centre of the pipe. The horizontal profile may be considered to represent the shape of the interface flow region C.

Further, a vertical profile may be generated by generating a numerical average of each row of data within the obtain data. FIG. 11c shows a plot of such a vertical profile. The horizontal axis shows the average intensity (not to scale) at each vertical location across the pipe (vertical axis). In the illustrated plot it can be seen that the conductivity profile peaks at a location approximately $\frac{1}{6}^{th}$ of the way up the pipe from the bottom, with a slight decay towards the bottom of the pipe, and a significant decay towards the top of the pipe. The vertical profile may be considered to represent the location of the interface flow region C.

Processing then passes to step S12 where various flow regions are identified. That is, the profiles generated at step S11 are used to assist with the identification of flow regions A, B and C within the pipe 3. For example, by considering the location of peak conductivity, the location of the interface region (flow region C) can be determined, with regions either side of this location being identified as the slurry (flow region A) and air (flow region B) regions respectively. Given prior knowledge that a slurry will flow in the lower portion of a pipe (due to gravity), while any air will be generally found at the upper portion of a pipe, those flow regions below and above the interface region can be identified as slurry (flow region A) and air (flow region B) respectively.

Moreover, it will be appreciated that in some cases the interface region may not lie exactly horizontally within the pipe and/or the centre of the flow region A may not lie at the centre of the pipe. The generated profiles allow any such deviation to be taken into account.

The extent and location of the interface region may be determined based upon known flow patterns. That is, empirical data may be used to generate an expected flow pattern, or reference pattern for a given set of materials and conditions. The use of vertical and horizontal profiles allows a comparison to be made between the obtained data and the reference pattern, and for each flow region to be identified.

In some embodiments, an interface region may, for example, be determined as being centred at the peak conductivity location, or at an inflection point of the profile. Further, the extent of the interface region may be determined to be a region around the peak conductivity region with conductivity within a predetermined percentage of the peak conductivity.

It will, of course, be appreciated that the obtained data may be rotated with respect to any particular axis system. As such, the obtained data may be rotated so as to allow analysis in terms of horizontal and vertical profiles. Indeed, the data illustrated in FIGS. 7 to 9 is rotated by approximately 120 degrees with respect to a vertical/horizontal axis system. On the other hand, any convenient profiles or coordinate system may be used (e.g. radial and polar coordinates and profiles).

Moreover, it will be appreciated that the techniques described above need not be limited to use in systems having stratified flow with three layers. Flow systems with other numbers of layers can also benefit from this technique. Similarly, systems which do not exhibit stratified flow can also be treated in this way, provided there are stable flow patterns which can be in some way characterised has having distinct flow regions or distinct portions within the pipe or other region of interest, each of those flow regions can be provided with an appropriate weighting or scaling factor, and identified, for example, by comparison with a reference pattern.

Once flows regions are identified at step S12, processing passes to step S13 where a flow mask is generated. As described above with reference to FIGS. 8a and 8b, the flow mask comprises a set of data in which each of the sub-regions is assigned a value which represents the contribution of that sub-region to the true concentration within the pipe. The values (scaling factors) assigned to sub-regions within each of the flow regions A, B and C are, in this example, 1, 0 and 0.2 respectively. However, it will be appreciated that these scaling factors can be selected so as to reflect the nature of a particular flow system. That is, as with the identification of the various flow regions, the scaling factors can be determined based upon empirical data.

Having generated the flow mask at step S13, processing passes to step S14 where the flow mask (and its constituent scaling factors) is (are) applied to the obtained conductivity data. As discussed above with reference to FIGS. 9a and 9b, the output of this step is a set of data in which each of the sub-regions now has a single numerical value associated with it which is based upon the obtained conductivity data, but multiplied by an appropriate scaling factor based upon the flow mask.

Processing then passes to step S15 where the conductivity data is converted to volumetric concentration data. This process may, for example, be carried out as described above with reference to FIG. 4 (and in particular step S6). It will be appreciated that sub-regions which have a zero conductivity value as a result of the application of the mask will be assigned a zero concentration value.

Processing then passes to step S16 where an average concentration value can be derived for the entire region within the pipe. For example, by taking a numerical average of each of the non-zero concentration values (i.e. those within sub-regions within flow regions A and C), a value which is representative of the average concentration of the material within those flow regions can be derived.

Processing then passes to step S17 where average concentration value is compensated based upon the proportion of the pipe which is filled by flow regions A and C. That is, by scaling the average concentration value according to the number of non-zero sub-regions within the mask as a fraction of the total number of sub-regions within the pipe, it is possible normalise the concentration value based upon the known pipe diameter or geometry. Finally, such a concentration value can be further processed at step S18 (in combination with specific gravity data) to generate data indicative of the density of material within the pipe 2. Again, such processing is described in more detail further above.

It will be appreciated that any of the processing described above with reference to FIGS. 1 to 5 may be carried out in combination with the processing of FIG. 10. Further, various processing steps described above may be performed in a different order. For example the generation of profiles (S11), identification of flow regions (S12), and generation and application of masks (S13 and S14) may be carried out upon concentration data rather than conductivity data with the conversion to concentration performed prior to performing those processing steps. Similarly, the conversion to concentration may be performed at a later stage (e.g. after performing a spatial average at step S16 or even compensation at S17).

More generally, the processing of FIG. 10 may be used in combination with conductivity data, and/or concentration data to allow a more accurate representation of the flow within in a pipe to be generated. In particular, the identification of flow regions, and application of scaling factors based upon the identified flow regions can be applied to any form of tomography data to enable certain regions to be disregarded where they can otherwise result in misleading output data. Such techniques have particular application where air regions are known to be present within pipelines.

It will further be appreciated, of course, that the identification of various regions within a region of interest as described above may be based upon data received from sources other than the EIT sensor 4. For example, the identification of sub-regions may be based upon data received from other forms of density measurement apparatus, ERT/ECT sensors, or more generally any system which generates data indicative of a property of a material at a plurality of sub-regions within a region of interest.

While various processes are described above as being carried out on controller 8, it will be appreciated that those processes may instead be carried out by any appropriate form of processor. Moreover, the processing described above may be carried out by a plurality of processors which are arranged to communication with one another. For example, part of the processing may be carried out by a processor associated with the EIT sensor 4, while another part of the processing may be carried out by another processor which is remote from the EIT sensor 4. Similarly, processing may be carried out in real-time (i.e. as data is acquired by the EIT sensor), or at a later time on stored data.

It is will be appreciated by one of ordinary skill in the art that the invention has been described by way of example only, and that the invention itself is defined by the claims. Numerous modifications and variations may be made to the exemplary design described above without departing from the scope of the invention as defined in the claims. For example, the precise shape, configuration and dimensions of the various components may be varied.

The described and illustrated embodiments are to be considered as illustrative and not restrictive in character, it being understood that only the preferred embodiments have been shown and described and that all changes and modifications that come within the scope of the inventions as defined in the claims are desired to be protected. In relation to the claims, it is intended that when words such as "a," "an," or "at least one," are used to preface a feature there is no intention to limit the claim to only one such feature unless specifically stated to the contrary in the claim. When the language "at least a portion" and/or "a portion" is used the item can include a portion and/or the entire item unless specifically stated to the contrary.

The invention claimed is:

1. A slurry density measurement system for measuring the density of a slurry within a region, the slurry density measurement system comprising:
    a plurality of electrodes arranged around the region;
    an energisation source arranged to apply an electrical signal to at least one of said electrodes;
    a monitor arranged to monitor an electrical parameter at at least one of said electrodes, the monitored electrical parameter being caused to change in response to flow of electrical current within the region;
    a processor arranged to:
        generate data indicative of the complex impedance of the slurry within the region based upon the monitored electrical parameter; and
        generate data indicative of the slurry density of the slurry based upon the data indicative of the complex impedance of the slurry; and
    a gas fraction probe, the gas fraction probe being configured to generate data indicative of the proportion of gas within the region.

2. The slurry density measurement system according to claim 1, wherein generating the data indicative of the complex impedance of the material is further based upon reference data, said reference data comprising an expected value of the monitored electrical parameter, the expected value being based upon a reference material having a predetermined electrical characteristic affecting said electrical parameter.

3. The slurry density measurement system according to claim 2, wherein generating data indicative of the slurry density of the slurry based upon the monitored electrical parameter comprises generating data indicative of the relative difference between the monitored electrical parameter and the expected value of the monitored electrical parameter.

4. The slurry density measurement system according to claim 2, wherein generating data indicative of the complex impedance of the material based upon the monitored electrical parameter comprises generating data indicative of the relative impedance of the material compared to the reference material.

5. The slurry density measurement system according to claim 1, wherein generating data indicative of the slurry density of the slurry based upon the data indicative of the complex impedance of the slurry comprises:
    generating data indicative of the concentration of a first component within the slurry based upon the complex impedance of the slurry and the complex impedance of the first component.

6. The slurry density measurement system according to claim 5, wherein generating data indicative of the slurry density of the slurry is further based upon the complex impedance of a second component.

7. The slurry density measurement system according to claim 1, wherein generating data indicative of composition of the slurry comprises generating data indicative of the modulus of the complex impedance of the slurry.

8. The slurry density measurement system according to claim 1, further comprising at least one sensor arranged to generate data indicative of a property of the slurry within the region, wherein generating data indicative of the slurry density of the slurry within the region is further based upon the data indicative of a property of the slurry.

9. The slurry density measurement system according to claim 8, wherein the sensor is a temperature sensor or a conductivity sensor.

10. The slurry density measurement system according to claim 1, wherein the data indicative of the slurry density of the slurry is generated based upon the data indicative of the proportion of gas within the region.

11. The slurry density measurement system according to claim 1, wherein data indicative of the slurry density of the slurry comprises a plurality values, each value being associated with a respective one of a plurality of sub-regions within the region.

12. The slurry density measurement system according to claim 1, wherein data indicative of the slurry density of the slurry comprises a spatial average of a plurality of values, each of the plurality of values being associated with a respective one of a plurality of sub-regions within the region.

13. The slurry density measurement system according to claim 1, wherein the energisation source is arranged to apply an alternating electrical signal between at least a first pair of said electrodes.

14. The slurry density measurement system according to claim 13, wherein the monitor is arranged to monitor a potential difference between at least a second pair of said electrodes, whilst the electrical signal is applied between the first pair of said electrodes.

15. An industrial processing apparatus, the industrial processing apparatus comprising a slurry density measurement system for measuring the density of a slurry within a region, the slurry density measurement system comprising:
   a plurality of electrodes arranged around the region;
   an energisation source arranged to apply an electrical signal to at least one of said electrodes;
   a monitor arranged to monitor an electrical parameter at at least one of said electrodes, the monitored electrical parameter being caused to change in response to flow of electrical current within the region; and
   a processor arranged to:
      generate data indicative of the complex impedance of the slurry within the region based upon the monitored electrical parameter; and
      generate data indicative of the slurry density of the slurry based upon the data indicative of the complex impedance of the slurry.

16. The industrial processing apparatus according to claim 15, wherein the industrial processing apparatus is a hydraulic conveying apparatus.

17. A method for measuring the slurry density of a slurry within a region, the method comprising:
   providing: a plurality of electrodes around the region; an energisation source; a monitor; and a processor;
   applying an electrical signal to at least one of said electrodes by the energisation source;
   monitoring an electrical parameter at at least one of said electrodes, the electrical parameter being caused to change in response to flow of electrical current within the region;
   generating, by the processor, data indicative of the complex impedance of the slurry within the region based upon the monitored electrical parameter;
   generating data indicative of the slurry density of the slurry based upon the data indicative of the complex impedance of the slurry; and
   controlling an industrial process based upon the data indicative of the slurry density of the slurry.

18. A method for measuring the slurry density of a slurry within a region, the method comprising: a
   providing: a plurality of electrodes around the region; an energisation source; a monitor; and a processor;
   applying an electrical signal to at least one of said electrodes by the energisation source;
   monitoring an electrical parameter at at least one of said electrodes, the electrical parameter being caused to change in response to flow of electrical current within the region;
   generating, by the processor, data indicative of the complex impedance of the slurry within the region based upon the monitored electrical parameter;
   generating data indicative of the slurry density of the slurry based upon the data indicative of the complex impedance of the slurry; and
   controlling hydraulic conveying based upon the data indicative of the slurry density of the slurry.

19. A slurry density measurement system for measuring the density of a slurry within a region, the slurry density measurement system comprising:
   a plurality of electrodes arranged around the region;
   an energisation source arranged to apply an electrical signal to at least one of said electrodes;
   a monitor arranged to monitor an electrical parameter at at least one of said electrodes, the monitored electrical parameter being caused to change in response to flow of electrical current within the region; and
   a processor arranged to:
      generate data indicative of the complex impedance of the slurry within the region based upon the monitored electrical parameter; and
      generate data indicative of the slurry density of the slurry based upon the data indicative of the complex impedance of the slurry, wherein data indicative of the slurry density of the slurry comprises a spatial average of a plurality of values, each of the plurality of values being associated with a respective one of a plurality of sub-regions within the region.

20. The slurry density measurement system according to claim 19, wherein generating the data indicative of the complex impedance of the material is further based upon reference data, said reference data comprising an expected value of the monitored electrical parameter, the expected value being based upon a reference material having a predetermined electrical characteristic affecting said electrical parameter.

* * * * *